United States Patent
Wang

(10) Patent No.: US 10,428,071 B2
(45) Date of Patent: Oct. 1, 2019

(54) CARBOLINE DERIVATIVE SERVING AS BROMODOMAIN INHIBITOR

(71) Applicant: NINGBO WENDA PHARMA TECHNOLOY LTD., Ningbo, Zhejiang (CN)

(72) Inventor: Nenghui Wang, Zhejiang (CN)

(73) Assignee: NINGBO WENDA PHARMA TECHNOLOY LTD., Ningbo, Zhejiang (CN)

( * ) Notice: Subject to any disclaimer, the term of this patent is extended or adjusted under 35 U.S.C. 154(b) by 0 days.

(21) Appl. No.: 16/071,666

(22) PCT Filed: Jan. 9, 2017

(86) PCT No.: PCT/CN2017/070640
§ 371 (c)(1),
(2) Date: Jul. 20, 2018

(87) PCT Pub. No.: WO2017/124936
PCT Pub. Date: Jul. 27, 2017

(65) Prior Publication Data
US 2019/0031660 A1 Jan. 31, 2019

(30) Foreign Application Priority Data
Jan. 20, 2016 (CN) .......................... 2016 1 0038402

(51) Int. Cl.
| | | |
|---|---|---|
| *C07D 471/14* | (2006.01) | |
| *A61K 31/437* | (2006.01) | |
| *C07D 471/04* | (2006.01) | |
| *A61P 37/04* | (2006.01) | |
| *A61P 31/12* | (2006.01) | |
| *A61P 35/02* | (2006.01) | |

(52) U.S. Cl.
CPC .......... *C07D 471/14* (2013.01); *A61K 31/437* (2013.01); *C07D 471/04* (2013.01); *A61P 31/12* (2018.01); *A61P 35/02* (2018.01); *A61P 37/04* (2018.01)

(58) Field of Classification Search
CPC ..................................................... C07D 471/14
USPC .......................................................... 546/65
See application file for complete search history.

(56) References Cited

U.S. PATENT DOCUMENTS

2016/0333013 A1    11/2016   Norris et al.

FOREIGN PATENT DOCUMENTS

| CN | 104860995 A    | 8/2015 |
| WO | 2015100282 A1  | 7/2015 |
| WO | 2016183114 A1  | 11/2016 |
| WO | 2016183115 A1  | 11/2016 |
| WO | 2016183118 A1  | 11/2016 |

OTHER PUBLICATIONS

International Search Report and Written Opinion; International Patent Application No. PCT/CN2017/070640, dated Apr. 14, 2017, with English translation of search report (16 pages).

*Primary Examiner* — Nizal S Chandrakumar
(74) *Attorney, Agent, or Firm* — Hamre, Schumann, Mueller & Larson, P.C.

(57) ABSTRACT

Disclosed in the present invention is a carboline derivative serving as an bromodomain inhibitor. The carboline derivative in the present invention can be used as an bromodomain inhibitor, and can provide a method and a pharmaceutical composition for controlling diseases intervened by a bromodomain protein.

2 Claims, No Drawings

CARBOLINE DERIVATIVE SERVING AS BROMODOMAIN INHIBITOR

FIELD OF THE INVENTION

The invention relates to a carboline derivative which acts as a bromodomain inhibitor.

BACKGROUND OF THE INVENTION

The eukaryotic genome is highly organized within the nucleus. The long-chain of double-stranded DNA twines the histone octamer (most commonly comprising two copies of histones H2A, H2B, H3, and H4) to form nucleosomes. Then, the basic unit is further compressed by nucleus aggregation and folding to form highly condensed chromatin structure. There are a series of possible different aggregation states, and the compactness of the structure changes during the cell cycle and is most compact during the cell division process. Chromatin structure plays a key role in the regulation of gene transcription, and gene transcription cannot occur efficiently by highly condensed chromatin. The chromatin structure is controlled by a series of post-translational modifications of histones (in particular histones H3 and H4), and the modification is most often within the tail of histone, the tail extends beyond the core nucleosome structure. These modifications include acetylation, methylation, phosphorylation, ubiquitination, and SUMOylation. These epigenetic marks are written and erased by specific enzymes. The specific enzyme will be tagged on specific residues in the tail of the histone, thus forming an epigenetic coding, which is then interpreted by the cell to allow the gene specific regulation of chromatin structure, thus allowing the transcription.

Histone acetylation is most commonly associated with the activation of gene transcription because this modification relaxes the interaction of DNA and histone octamers by altering the electrostatic properties. In addition to this physical change, specific proteins bind to acetylated lysine residues within histones to read epigenetic coding. In the case of histones, the bromodomains are small, distinct domains within a protein that are normally but not specifically bound to acetylated lysine residues. There is a family of about 50 proteins that are known to contain bromodomains and they have a range of functions within the cell.

The bromodomain-containing protein of Bet family includes four kinds of proteins (BRD2, BRD3, BRD4, and BRD-t) having tandem bromodomain domain that can bind two closely acetylated lysine residues, thus increasing the specificity of the interaction. It has been reported that BRD2 and BRD3 bind to histones along actively transcribed genes and may be involved in promoting transcriptional extension (Leroy et al., Mol. Cell. 2008 30(1):51-60), while BRD4 seems to be involved in the recruite of pTEF-I3 complex to inducible genes, thus resulting in phosphorylation of RNA polymerase and increased transcriptional output (Hargreaves et al., 2009, 138(1): 129-145). Moreover, all family members have certain functions in the control or execution of the cell cycle, and have been shown to maintain their recombination with chromosomes during cell division, which suggests their role in maintaining epigenetic memory. In addition, as part of the viral replication process, some viruses utilize these proteins to tether their genomes to the chromatin of the host cells (You et al., Cell, 2004 117(3): 349-60).

Related recent articles include Trends in Molecular Medicines about BET (2014, 20(9) 477-478); Trends in Pharmacological Sciences (2012, 33(3)146-153); J. Med. Chem., (2012, 55, 9393-9413); J. Biol. Chem., (2012, 287(46): 38956). Hundreds of different genetic factors are identified, many of which are chromatin-associated proteins. These associated proteins are directly related to different diseases such as cancer, neurological diseases, metabolic diseases, cardiovascular diseases, viruses, inflammation, autoimmune diseases and the like. The clinically developed bromodomain inhibitors include BMS-986158 (BMS), MRK-8628 (Merck), BAY1238097 (Bayer), INCB54329 (Incyte), etc. Therefore, the bromodomain inhibitor provided by the present invention can provide a method for controlling the pathological changes involved by the bromodomain protein.

SUMMARY OF THE INVENTION

The purpose of the invention is to provide a carboline derivative as a bromodomain inhibitor.

In the first aspect of the invention, a carboline derivative, or the pharmaceutically acceptable salts, solvates, stereoisomers, or tautomers thereof are provided, wherein the structure of the carboline derivative is of formula I:

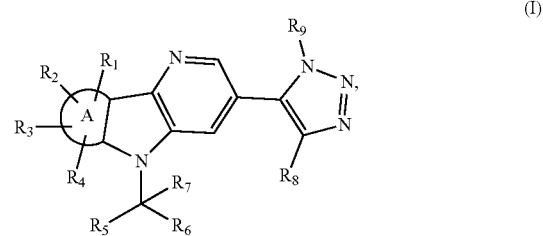

wherein,

A is aryl, heteroaryl, or 3- to 12-membered monocyclic or polycyclic heterocyclic ring, wherein the heterocyclic ring contains 0-4 (preferably 1 to 3) heteroatoms each independently being N, O, S, S(O) or S(O)$_2$;

$R_1$, $R_2$, $R_3$ and $R_4$ are each independently hydrogen, halogen, $C_{1-8}$ alkyl, $C_{2-8}$ alkenyl, $C_{2-8}$ alkynyl, $C_{3-8}$ cycloalkyl, $C_{1-8}$ alkoxy, $C_{1-8}$ alkoxy carbonyl, $C_{3-8}$ epoxyalkyl, aryl, heteroaryl, or 3- to 12-membered heterocyclic group; or the adjacent $R_1$, $R_2$, $R_3$, $R_4$ together with the atom of A ring attached with them form 3- to 9-membered ring;

$R_5$ is selected from the group consisting of hydrogen, halogen, $C_{1-8}$ alkyl, $C_{2-8}$ alkenyl, $C_{2-8}$ alkynyl, $C_{3-8}$ cycloalkyl, $C_{1-8}$ alkoxy, $C_{1-8}$ alkoxy carbonyl, aryl, heteroaryl, or 3- to 12-membered heterocyclic group;

$R_6$ is selected from the group consisting of hydrogen, halogen, $C_{1-8}$ alkyl, $C_{2-8}$ alkenyl, $C_{2-8}$ alkynyl, $C_{3-8}$ cycloalkyl, $C_{1-8}$ alkoxy, $C_{1-8}$ alkoxy carbonyl, aryl, heteroaryl, or 3- to 12-membered heterocyclic group;

$R_7$ is selected from the group consisting of hydrogen, halogen, $C_{1-8}$ alkyl, $C_{2-8}$ alkenyl, $C_{2-8}$ alkynyl, $C_{3-8}$ cycloalkyl, $C_{1-8}$ alkoxy, $C_{1-8}$ alkoxy carbonyl, aryl, heteroaryl, or 3- to 12-membered heterocyclic group;

$R_8$ is selected from the group consisting of hydrogen, halogen, $C_{1-8}$ alkyl, $C_{2-8}$ alkenyl, $C_{2-8}$ alkynyl, $C_{3-8}$ cycloalkyl, $C_{1-8}$ alkoxy, $C_{1-8}$ alkoxy carbonyl;

$R_9$ is selected from the group consisting of hydrogen, halogen, $C_{1-8}$ alkyl, $C_{2-8}$ alkenyl, $C_{2-8}$ alkynyl, $C_{3-8}$ cycloalkyl, $C_{1-8}$ alkoxy, $C_{1-8}$ alkoxy carbonyl;

wherein each of the above-mentioned alkyl, alkenyl, alkynyl, cycloalkyl, heterocyclic group, aryl, heteroaryl, 3- to 9-membered ring is optionally and each independently substituted with one or more substituents, and the substituents are each independently halogen, halogen, $C_{1-8}$ alkyl, $C_{2-8}$ alkenyl, $C_{2-8}$ alkynyl, $C_{3-8}$cycloalkyl, 3- to 12-membered heterocyclic group, aryl, heteroaryl, CN, $NO_2$, =O, or =S.

In another preferred embodiment, the structure of the carboline derivative is shown in the following Formula II:

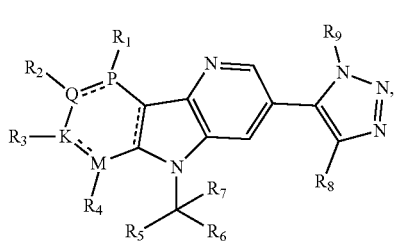
(II)

wherein P, Q, K and M are each independently N or C;
"═" represents single bond or double bond;
$R_1$, $R_2$, $R_3$, $R_4$, $R_5$, $R_6$, $R_7$, $R_8$, $R_9$ are each defined as above.

In another preferred embodiment, P is N.
In another preferred embodiment, Q is N.
In another preferred embodiment, K is N.
In another preferred embodiment, each substitution refers to being substituted by 1 to 6 substituents, preferably 1 to 3 substituents.

In another preferred embodiment, the 3- to 9-membered ring optionally contains 1-3 heteroatoms selected from N, O, and S.

In another preferred embodiment, the 3- to 9-membered ring is saturated or unsaturated.

In another preferred embodiment, $R_1$ and $R_2$ together with the carbon atom to which they are attached form a 3- to 9-membered ring, preferably a 5-membered ring or a 6-membered ring.

In another preferred embodiment, $R_2$ and $R_3$ together with the carbon atom to which they are attached form a 3- to 9-membered ring, preferably a 5-membered ring or a 6-membered ring.

In another preferred embodiment, $R_4$ is selected from the group consisting of hydrogen, halogen, $C_{1-3}$ alkyl, $C_{2-4}$ alkenyl, $C_{2-4}$ alkynyl, $C_{1-5}$ alkoxy;

In another preferred embodiment, $R_5$ is selected from the group consisting of $C_{3-8}$ epoxyalkyl, aryl, and heteroaryl.

In another preferred embodiment, $R_6$ is selected from the group consisting of aryl, heteroaryl, and 3- to 12-membered heterocyclic group.

In another preferred embodiment, the 3- to 12-membered ring is saturated or unsaturated, and contains 1, 2, or 3 heteroatoms selected from N, O, and S.

In another preferred embodiment, $R_7$ is selected from the group consisting of hydrogen, halogen, $C_{1-3}$ alkyl, $C_{2-4}$ alkenyl, $C_{2-4}$ alkynyl, $C_{1-5}$ straight or branched alkoxy;

In another preferred embodiment, $R_8$ is selected from the group consisting of hydrogen, halogen, $C_{1-8}$ deuterated alkyl, $C_{2-4}$ alkenyl, $C_{2-4}$ alkynyl.

In another preferred embodiment, $R_8$ is selected from the group consisting of hydrogen, halogen, $C_{1-3}$ deuterated alkyl, $C_{2-4}$ alkenyl, $C_{2-4}$ alkynyl.

In another preferred embodiment, $R_8$ is deuterated methyl.

In another preferred embodiment, $R_9$ is selected from the following group: $C_{1-3}$ alkyl, $C_{2-8}$ alkenyl, $C_{2-8}$ alkynyl, $C_{3-8}$ cycloalkyl, $C_{1-5}$ alkoxy.

In another preferred embodiment, the chiral carbon atom in the compound of formula (I) is R type and/or S type.

In another preferred embodiment, the carboline derivative is selected from the group consisting of:

| Number of the compound | Structure |
|---|---|
| 1 | ![structure 1] |
| 2 | ![structure 2] |
| 3 | ![structure 3] |
| 4 | ![structure 4] |

US 10,428,071 B2

5
-continued

| Number of the compound | Structure |
|---|---|
| 5 | 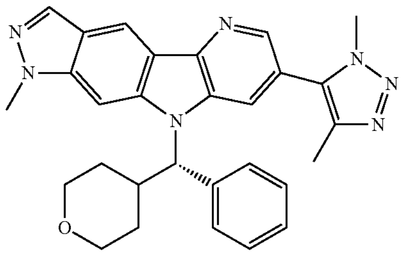 [SMILES: Cc1nnn(C)c1-c1cnc2c3cc4cnn(C)c4cc3n([C@H](c3ccccc3)C3CCOCC3)c2c1] |
| 6 | 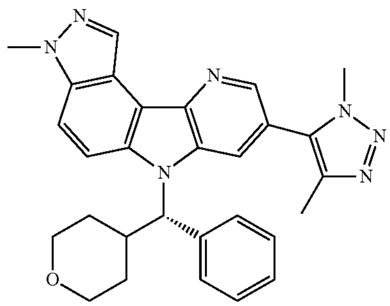 [SMILES: Cc1nnn(C)c1-c1cnc2c3c4cnn(C)c4ccc3n([C@H](c3ccccc3)C3CCOCC3)c2c1] |
| 7 | 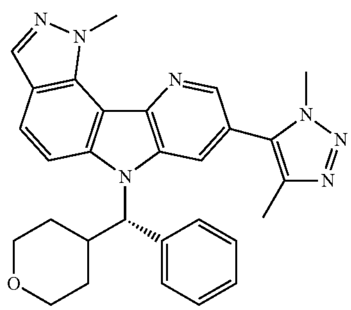 [SMILES: Cc1nnn(C)c1-c1cnc2c3c4c(ccc3n([C@H](c3ccccc3)C3CCOCC3)c2c1)cnn4C] |
| 8 | 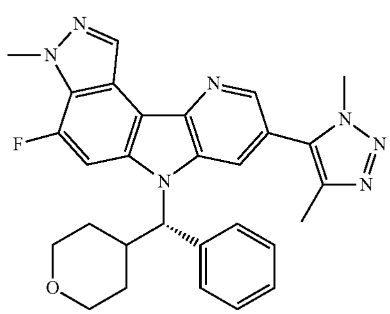 [SMILES: Cc1nnn(C)c1-c1cnc2c3c4cnn(C)c4c(F)cc3n([C@H](c3ccccc3)C3CCOCC3)c2c1] |
| 9 | 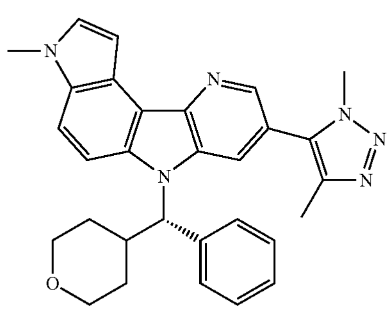 [SMILES: Cc1nnn(C)c1-c1cnc2c3c4ccn(C)c4ccc3n([C@H](c3ccccc3)C3CCOCC3)c2c1] |

6
-continued

| Number of the compound | Structure |
|---|---|
| 10 | |
| 11 | |
| 12 | |
| 13 | |

| Number of the compound | Structure |
|---|---|
| 14 | 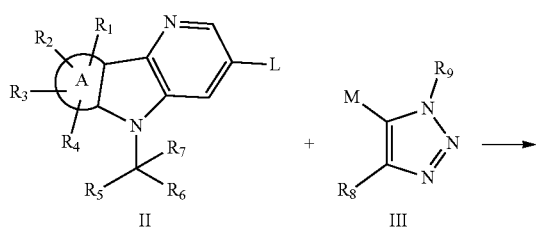 |

In the second aspect of the present invention, a pharmaceutical composition is provided, which comprises: (i) therapeutically effective amount of compound of the first aspect of the invention, or the pharmaceutically acceptable salt thereof, and (ii) pharmaceutically acceptable carrier(s).

In the third aspect of the present invention, the use of compound I of the first aspect of the present invention or the pharmaceutically acceptable salt is provided in:

(a) the preparation of bromodomain inhibitors;

(b) the preparation of drugs for the prevention and/or treatment of diseases related to the bromodomain; and/or (c) in vitro non-therapeutic inhibition of bromodomain;

In another preferred embodiment, the disease is selected from the group consisting of cancers, neurogenic diseases, metabolic diseases, cardiovascular diseases, viral infections, inflammation, tissue fibrosis-related diseases, and autoimmune diseases.

In another preferred embodiment, the tumor is selected from the group consisting of lung cancer, breast cancer, blood cancer, cervical cancer, ovarian cancer, intestinal cancer, pancreatic cancer, prostate cancer, liver cancer, brain tumor, skin cancer, other solid tumors and the like.

In the fourth aspect of the present invention, a method of inhibiting bromodomain is provided, which comprising steps: administering an inhibitory effective amount of formula I compound of the first aspect of the present invention or a pharmaceutically acceptable salt thereof to an inhibition subject, or administering an inhibitory effective amount of the pharmaceutical composition of the second aspect of the present invention to an inhibition subject.

In the fifth aspect of the present invention, the preparation method of the compound of the first aspect of the present invention is provided, which comprises the following step:

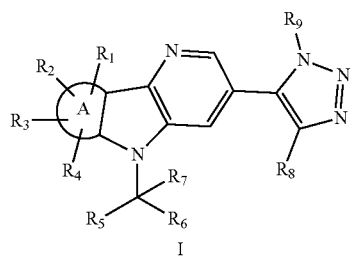

(1) Reacting compound of Formula II with compound of Formula III to provide compound of Formula I, wherein L is a leaving group, and M is a group that can be coupled to L.

In another preferred embodiment, the method further comprises the following step:

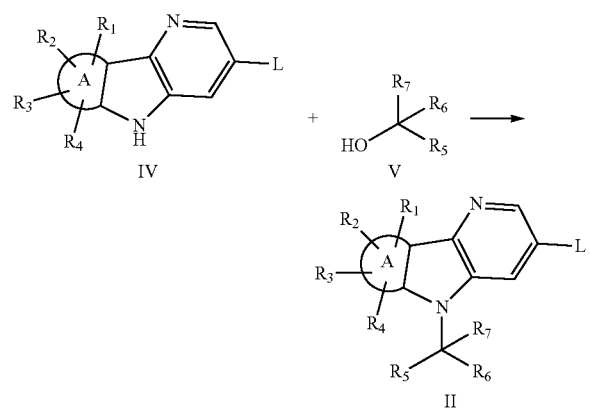

(2) Reacting compound of Formula IV with compound of Formula V to provide compound of Formula II, wherein L is a leaving group.

In another preferred embodiment, the method further comprises the following step:

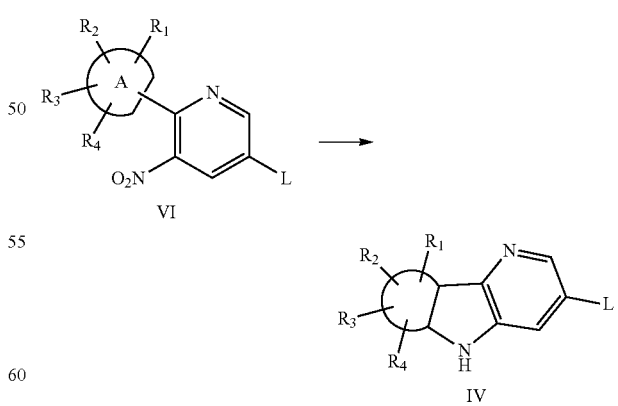

(3) Preparing compound of Formula IV by compound of Formula VI.

In another preferred embodiment, the method further comprises the following step:

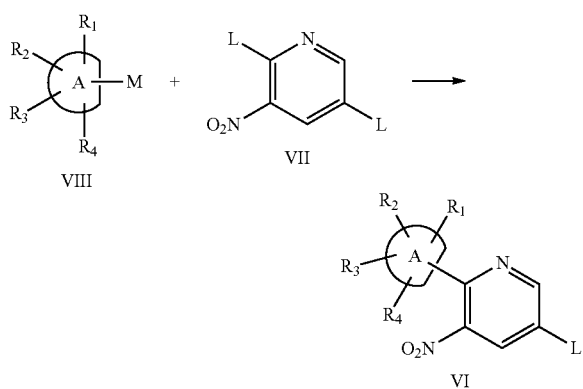

(4) Reacting compound of formula VIII with compound of formula VII to provide compound of formula VI, wherein L is a leaving group and M is a group that can be coupled to L.

In another preferred embodiment, the method further comprises the following step:

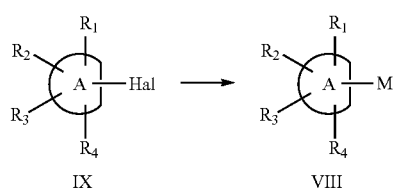

(5) Preparing compound of formula VIII by compound of formula IX, wherein Hal is halogen, M is as described above.

In another preferred embodiment, L is halogen group.
In another preferred embodiment, M is boric acid or borate ester group.
In another preferred embodiment, the method comprises the following step:

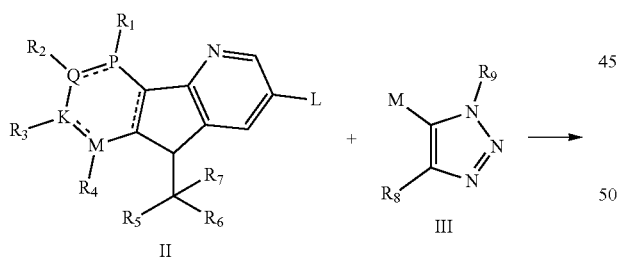

(1) Reacting compound of Formula II with compound of Formula III to provide compound of Formula I, wherein L is a leaving group, and M is a group that can be coupled to L.

In another preferred embodiment, the method further comprises the following step:

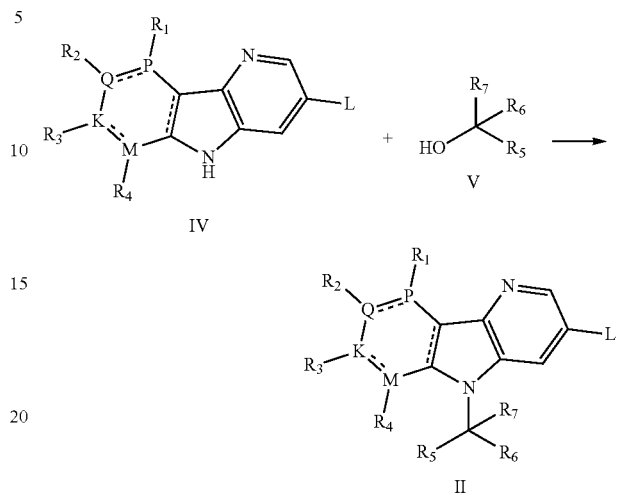

(2) Reacting compound of Formula IV with compound of Formula V to provide compound of Formula II, wherein L is a leaving group.

In another preferred embodiment, the method further comprises the following step:

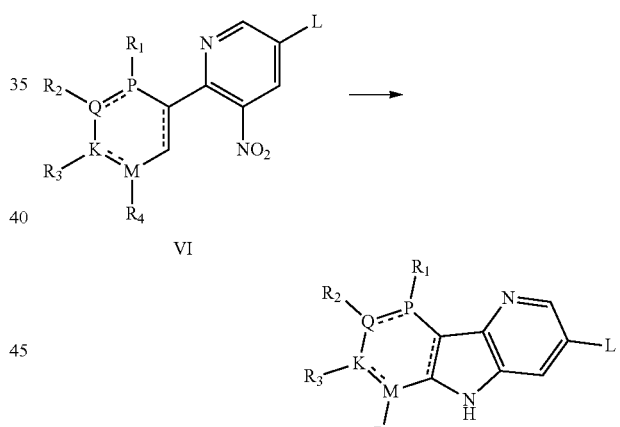

(3) Preparing compound of Formula IV by compound of Formula VI.

In another preferred embodiment, the method further comprises the following step:

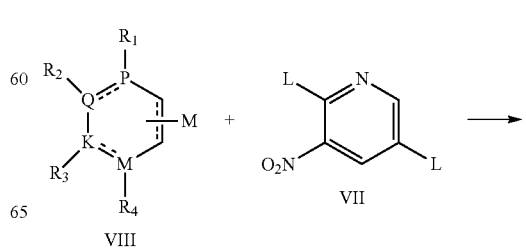

-continued

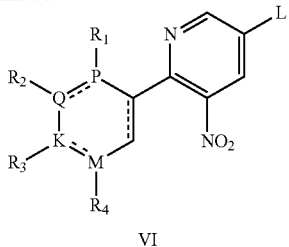

VI (4) Reacting compound of formula VIII with compound of formula VII to provide compound of formula VI, wherein L is a leaving group and M is a group that can be coupled to L.

In another preferred embodiment, the method further comprises the following step:

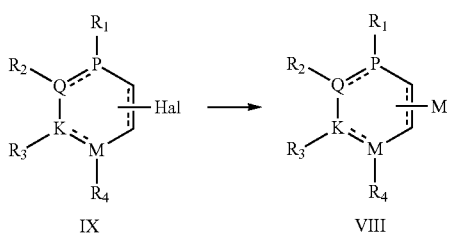

(5) Preparing compound of formula VIII by compound of formula IX, wherein Hal is halogen, M is as described above.

It should be understood that, in the present invention, each of the technical features specifically described above and below (such as those in the Examples) can be combined with each other, thereby constituting new or preferred technical solutions which need not be specified again herein.

EMBODIMENTS FOR CARRYING OUT THE INVENTION

Through extensive and intensive study, the inventor has developed a novel carboline derivative having the structure shown in Formula I for the first time, which can be used as a bromodomain inhibitor. The present invention is completed on this basis.

Terms

Unless otherwise stated, "or" as used herein has the same meaning as "and/or" (refers to "or" and "and").

Unless otherwise stated, in compounds of the present invention, each chiral carbon atom (chiral center) may optionally be in R configuration or S configuration, or the mixture of R configuration and S configuration.

As used herein, the term "alkyl", alone or as part of another substituent, refers to a straight (i.e., unbranched) or branched alkyl group having from 1 to 8 carbon atoms, or a combination thereof. The alkyl group can be saturated, monounsaturated or polyunsaturated, and can include divalent or multivalent radicals. When the alkyl group has a carbon number limitation (e.g., $C_{1-10}$), it means that the alkyl group has 1 to 10 carbon atoms. For example, the $C_{1-8}$ alkyl group may be a linear or branched alkyl having 1 to 8 carbon atoms, such as methyl, ethyl, propyl, isopropyl, butyl, isobutyl, sec-butyl, tert-butyl, or similar groups.

As used herein, the term "alkenyl", alone or as part of another substituent, refers to a straight or branched carbon chain having at least one carbon-carbon double bond. The alkenyl group having one double bond may be represented by $—C_nH_{2n-1}$, and the alkenyl group having 2 double bonds may be represented by $—C_nH_{2n-3}$. When the alkenyl group has a carbon number limitation (e.g., $C_{2-8}$), it means that the alkenyl group has 2-8 carbon atoms, for example, a straight or branched alkenyl group having 2-8 carbon atoms, such as ethenyl, propenyl, 1,2-butenyl, 2,3-butenyl, butadienyl, or the like.

As used herein, the term "alkynyl", alone or as part of another substituent, refers to an aliphatic hydrocarbon group having at least one carbon-carbon triple bond. The alkynyl group can be straight or branched, or a combination thereof. In some embodiments, the alkynyl group has 2-12 (e.g., 2-8, 2-6, or 2-4) carbon atoms. When the alkynyl group has a carbon number limitation (e.g., $C_{2-8}$ alkynyl), it means that the alkynyl group has 2-8 carbon atoms. For example, the term "$C_{2-8}$ alkynyl" means a straight or branched alkynyl group having 2 to 8 carbons, such as ethynyl, propynyl, isopropynyl, butynyl, isobutynyl, sec-butynyl, tert-butynyl, or the like.

As used herein, the term "cycloalkyl", alone or as part of another substituent, refers to saturated or partially saturated monocyclic, bicyclic or tricyclic (including cyclo, bridged or spiro) ring. The cycloalkyl group may have 3 to 12 (for example, 3 to 10, or 5 to 10) carbon atoms. When a certain cycloalkyl group has a carbon number limitation (e.g., $C_{3-10}$), it means that the cycloalkyl group has 3 to 10 carbon atoms. In some preferred embodiments, the term "$C_{3-8}$ cycloalkyl" refers to a saturated or partially saturated monocyclic or bicyclic alkyl group having from 3 to 8 carbon atoms, such as cyclopropyl, cyclobutyl, cyclopentyl, cycloheptyl, or the like.

As used herein, the term "alkoxy" or "alkyloxy" refers to an alkyl group attached through an oxygen atom (e.g., —O-alkyl), wherein alkyl is as defined above. Examples of specific alkoxy groups are, for example (but not limited to), methoxy, ethoxy, propoxy, isopropoxy, butoxy, isobutoxy, sec-butoxy, tert-butoxy, or the like. The alkoxy group may be substituted by one or more substituents, such as a halogen, an amino group, a cyano group, or a hydroxyl group. The alkoxy group can be straight or branched. When the alkoxy group has a carbon number limitation (e.g., $C_{1-8}$), it means that the cycloalkyl group has 1-8 carbon atoms.

As used herein, the term "halogen", alone or as part of another substituent, refers to F, Cl, Br, or I.

As used herein, the term "alkoxycarbonyl" refers to a straight or branched alkyl-oxycarbonyl moiety (alkoxy-C=O). The alkoxy group may have 1 to 8 carbon atoms. When the alkoxycarbonyl group has a carbon number limitation (for example, $C_{1-8}$), it means that the alkyl moiety of the alkoxycarbonyl group has 1-8 carbon atoms, for example, a $C_{1-8}$ alkoxycarbonyl group means a group of "$C_{1-8}$ alkoxy-C=O—" structure, such as a methoxycarbonyl group, an ethoxycarbonyl group, a tert-butoxycarbonyl group, or the like.

As used herein, the term "aryl", alone or as part of another substituent, refers to a monocyclic, bicyclic or fused cyclic aromatic hydrocarbon group. The aryl group may be substituted or unsubstituted. When an aryl group has a carbon number limitation (e.g., $C_{6-12}$), it means that the aryl group has 6 to 12 carbon atoms. Examples of aryl groups are, for example (but not limited to), phenyl, biphenyl, naphthyl, or the like (each of which may be optionally substituted). In the present invention, the aryl group is preferably a $C_{6-12}$ aryl group.

As used herein, the term "heteroaryl", alone or as part of another substituent, refers to a monocyclic, bicyclic or fused cyclic aromatic group having a particular number of ring carbon atoms (e.g., $C_{4-10}$ means 4 to 10 ring-forming carbon atoms) and includes at least one same or different hetero atom selected from N, O and S. Each ring atom can be arbitrarily substituted. The heteroaryl group may be 5- to 15-membered, having 1 to 5 aromatic ring groups each independently selected from the hetero atoms of N, O and S. Examples of heteroaryl groups are, for example (but not limited to), pyridine, pyrimidine, pyrrole, oxazole, indole, furan, benzofuran, thiophene, or the like.

As used herein, the term "heterocyclic group", alone or as part of another substituent, refers to a monocyclic or fused cyclic saturated or partially saturated substituents, which have a particular number of ring carbon atoms (e.g., $C_{3-11}$ means 3 to 11 ring-forming carbon atoms) and includes at least one same or different hetero atom selected from N, O and S. In the present invention, the heterocyclic group may be a 3- to 15-membered heterocyclic group having 1 to 5 hetero atoms each independently selected from N, O and S. Examples of the heterocyclic group are, for example, but not limited to, a nitrogen heterocyclic group, an oxygen heterocyclic group, a sulphur heterocyclic group, a nitrogen oxygen heterocyclyl group, a nitrogen sulphur heterocyclic group, an oxygen sulphur heterocyclic group and the like, and more preferrably the heterocyclic groups appearing in the various examples of the present application. In the present invention, the heterocyclic group may be monocyclic, bicyclic or tricyclic (including fused ring, bridged ring or spiro ring).

As used herein, the term "arbitrarily" or "optionally" (e.g., "optionally substituted") means that the moiety is substituted or unsubstituted, and that the substitution occurs only on a chemically achievable position. For example, H, a covalent bond or a —C(=O)— group may not be substituted by a substituent.

As used herein, "oxy" or "oxyl" refers to =O.

As used herein, unless otherwise specified, the term "pharmaceutically acceptable salt" refers to a salt that is suitable for contact with the tissue of a subject (e.g., human) without causing unpleasant side effects. In some embodiments, a pharmaceutically acceptable salt of a compound of the invention includes a salt of a compound of the invention having an acidic group (e.g., a potassium salt, a sodium salt, a magnesium salt, a calcium salt) or a salt of a compound of the invention having an alkali group (for example, a sulfate, a hydrochloride, a phosphate, a nitrate, a carbonate).

As used herein, the term "substituted" (when with or without "optionally") means that one or more hydrogen atoms on a particular group are replaced by a specific substituent. The specific substituent is a substituent which is correspondingly described in the foregoing, or a substituent which appears in each embodiment. Unless otherwise indicated, an optionally substituted group may have a substituent selected from a particular group at any substitutable position of the group, wherein the substituents may be the same or different at each position. A cyclic substituent, such as a heterocycloalkyl group, may be attached to another ring, such as a cycloalkyl group, to form a spirobicyclic ring system, for example, two rings having a common carbon atom. Those skilled in the art will appreciate that the combinations of substituents contemplated by the present invention are those that are stable or chemically achievable.

The substituents are, for example but not limited to, deuterium, $C_{1-8}$ alkyl, $C_{2-8}$ alkenyl, $C_{2-8}$ alkynyl, $C_{3-8}$ cycloalkyl, 3- to 12-membered heterocyclic group, aryl, heteroaryl, halogen, hydroxy, carboxy (—COOH), $C_{1-8}$ aldehyde, $C_{2-10}$ acyl, $C_{2-10}$ ester group, amino. In the present invention, the deuterated alkyl group may be perdeuterated, partially deuterated, or a mixture thereof.

For convenience and in accordance with conventional understanding, the term "optional substituted" or "optionally substituted" applies only to sites which are capable of being substituted by a substituent, and does not include those which are not chemically achievable.

Pharmaceutically Acceptable Salts, Solvates, Stereoisomers, Tautomers

As used herein, the term "pharmaceutically acceptable salts" refers to salts formed by a compound of the present invention with a pharmaceutically acceptable inorganic or organic acids, wherein the preferable inorganic acids include (but are not limited to): hydrochloric acid, hydrobromic acid, phosphoric acid, nitric acid, sulfuric acid; the preferable organic acids include (but are not limited to): formic acid, acetic acid, propionic acid, succinic acid, naphthalene disulfonic acid (1,5), asiatic acid, oxalic acid, tartaric acid, lactic acid, salicylic acid, benzoic acid, valeric acid, diethyl acetic acid, malonic acid, succinic acid, fumaric acid, pimelic acid, adipic acid, maleic acid, malic acid, sulfamic acid, phenylpropionic acid, gluconic acid, ascorbic acid, nicotinic acid, isonicotinic acid, methanesulfonic acid, p-toluenesulfonic acid, citric acid, and amino acids.

As used herein, the term "pharmaceutically acceptable solvate" refers to a solvate of a compound of the present invention with a pharmaceutically acceptable solvent, wherein the pharmaceutically acceptable solvent includes (but is not limited to): water, ethanol, methanol, isopropanol, tetrahydrofuran, dichloromethane.

As used herein, the term "pharmaceutically acceptable stereoisomer" means that the chiral carbon atoms involved in the compounds of the present invention may in R configuration, S configuration, or a combination thereof.

Pharmaceutical Composition

The present invention also provides a pharmaceutical composition which has a significant anti-tumor effect, and the composition comprises a therapeutically effective acceptable amount of a compound of formula I, or a pharmaceutically acceptable salt thereof, and one or more pharmaceutically acceptable carriers.

The mixture of the compound or the pharmaceutically acceptable salts thereof and pharmaceutically acceptable excipients, diluents and the like can be administered in tablet, capsule, granule, powder or syrup forms for oral administration, or in injection formulations for non-oral administration. The pharmaceutical composition preferably comprises 0.01%-99% in weight ratio of the compound of formula I in the present invention or the pharmaceutically acceptable salts thereof as an active ingredient, more preferably 0.1%-90% in weight ratio of the active ingredient.

The above formulations may be prepared by conventional pharmacy methods. Examples of acceptable adjuvants can be used include excipients (e.g. sugar derivatives such as lactose, sucrose, glucose, mannitol and sorbitol; starch derivatives such as corn starch, potato starch, dextrin and carboxymethyl starch; cellulose derivatives such as crystalline cellulose, hydroxypropyl cellulose, carboxymethyl cellulose, calcium carboxymethyl cellulose, sodium carboxymethyl cellulose; arabic gum; dextranum; silicate derivatives such as magnesium aluminum metasilicate; phosphate derivatives such as calcium phosphate; carbonate derivatives such as calcium carbonate; sulfate derivatives such as calcium sulfate, etc.), binders (e.g., gelatin, polyvinyl pyrrolidone, and polyethylene glycols), disintegrants (e.g., cellulose derivatives such as sodium carboxymethyl cellulose, polyvinylpyrrolidone), lubricants (e.g., talc, calcium stearate, magnesium stearate, spermaceti, boric acid, sodium benzoate, leucine), stabilizers (methyl parahydroxybenzoate, propyl para-hydroxybenzoate, etc.), flavoring agents (such as the commonly used sweeteners, sour agents and spices and the like), diluents and solvents for injections (such as water, ethanol and glycerol, etc.).

The administrating dosage of compounds of the present invention, pharmaceutically acceptable salts or prodrugs thereof, or their pharmaceutical compositions varies with age, sex, race, and disease of the patients.

Pharmaceutical Composition and the Administration Thereof

The compounds of the present invention possess outstanding activity of inhibiting bromodomain. Therefore, the compound of the present invention, and the crystal forms, pharmaceutically acceptable inorganic or organic salts, hydrates or solvates thereof, and the pharmaceutical composition comprising the compounds of the present invention as a main active ingredient can be used for treating, preventing and alleviating diseases related to bromodomain activity or expression. According to the prior art, the compounds of the present invention can be used in the treatment of (but not limited to) the following diseases: various cancers, such as lung cancer, bladder cancer, breast cancer, stomach cancer, liver cancer, salivary adenoma, ovarian cancer, prostate cancer, cervical cancer, epithelium cancer, multiple myeloma, pancreatic cancer, lymphoma, chronic myelogenous leukemia, lymphocytic leukemia, cutaneous T cell lymphoma, etc.; T cell regulated inflammation and autoimmune diseases, such as rheumatoid arthritis, collagen II Arthritis, multiple sclerosis, systemic lupus erythematosus, psoriasis, juvenile-onset diabetes, sicca syndrome, thyroid disease, sarcoidosis, inflammatory bowel disease, celiac disease, and the like; and other neurological diseases, metabolic diseases, cardiovascular diseases, viral infections, inflammation, tissue fibrosis-related diseases, and the like.

The pharmaceutical composition of the invention comprises the compound of the present invention or the pharmacologically acceptable salts thereof in a safe and effective dosage range and pharmacologically acceptable excipients or carriers, in which the "safe and effective dosage" means that the amount of compound is sufficient to significantly ameliorate the condition without causing significant side effects. Generally, the pharmaceutical composition contains 1-2000 mg of the compound of the invention per dose, preferably, 5-200 mg of the compound of the invention per dose. Preferably, the "dose" is a capsule or tablet.

"Pharmaceutically acceptable carrier" means one or more compatible solid or liquid fillers, or gelatinous materials which are suitable for human use and should be of sufficient purity and sufficiently low toxicity. "Compatibility" means that each component in the composition can be admixed with the compounds of the present invention and with each other without significantly reducing the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

There is no special limitation of administration mode for the compounds or pharmaceutical compositions of the present invention, and the representative administration mode includes (but is not limited to): oral, intratumoral, rectal, parenteral (intravenous, intramuscular or subcutaneous), and topical administration.

Solid dosage forms for oral administration include capsules, tablets, pills, powders and granules. In these solid dosage forms, the active compounds are mixed with at least one conventional inert excipient (or carrier), such as sodium citrate or dicalcium phosphate, or mixed with any of the following components: (a) fillers or compatibilizer, for example, starch, lactose, sucrose, glucose, mannitol and silicic acid; (b) binders, for example, hydroxymethyl cellulose, alginates, gelatin, polyvinylpyrrolidone, sucrose and arabic gum; (c) humectant, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) absorption accelerators, for example, quaternary ammonium compounds; (g) wetting agents, such as cetyl alcohol and glyceryl monostearate; (h) adsorbents, for example, kaolin; and (i) lubricants such as talc, calcium stearate, magnesium stearate, solid polyethylene glycol, sodium lauryl sulfate, or the mixtures thereof. For capsules, tablets and pills, the dosage forms may also contain buffering agents.

The solid dosage forms such as tablets, sugar pills, capsules, pills and granules can be prepared by using coating and shell materials, such as enteric coatings and any other materials known in the art. They can contain an opaque agent. The active compounds or compounds in the compositions can be released in a delayed mode in a certain portion of the digestive tract. Examples of the embedding components include polymers and waxes. If necessary, the active compounds and one or more above excipients can form microcapsules.

Liquid dosage forms for oral administration include pharmaceutically acceptable emulsions, solutions, suspensions, syrups or tinctures. In addition to the active compounds, the liquid dosage forms may contain any conventional inert diluents known in the art such as water or other solvents, solubilizers and emulsifiers, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the combination thereof.

Besides these inert diluents, the composition may also contain additives such as wetting agents, emulsifiers, and suspending agents, sweeteners, flavoring agents and speices.

In addition to the active compounds, the suspension may contain suspending agent, for example, ethoxylated isooctadecanol, polyoxyethylene sorbitol and sorbitan esters, microcrystalline cellulose, methanol aluminum and agar, or the combination thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

The dosage forms of compounds of the invention for topical administration include ointments, powders, patches, aerosol, and inhalants. The active ingredients are mixed with physiologically acceptable carriers and any preservatives, buffers, or propellant if necessary, under sterile conditions.

Compounds of the present invention can be administrated alone, or in combination with any other pharmaceutically acceptable compounds.

When the pharmaceutical compositions are used, a safe and effective amount of the compound of the present invention is applied to a mammal (such as human) in need of, wherein the dose of administration is a pharmaceutically effective dose. For a person weighed 60 kg, the daily dose is usually 1-2000 mg, preferably 5-500 mg. Of course, the particular dose should also depend on various factors, such as the route of administration, patient's healthy status, which are well within the skills of an experienced physician.

Preparation Method

The carboline derivative according to the present invention can be prepared by various methods well-known to those skilled in the art and in the organic synthetic chemistry field. The compounds of the present invention can be synthesized by the methods described hereinafter, together with those known synthetic methods in the field of organic chemistry or variations thereon as understood by those skilled in the art.

The process for the preparation of the compounds of formula I according to the invention makes it possible to prepare the compounds according to the invention by the following general methods and processes from readily available starting materials. It will be understood that where typical or preferred process operating conditions (i.e., reaction temperature, time, moles of reactants, solvent, pressure, etc.) are given, other process operating conditions may also be used unless otherwise stated. Optimum reaction conditions may vary with the particular reactants or solvents used, but these conditions can be determined by one skilled in the art by routine optimization procedures.

The methods described herein for the compounds of Formula I of the present invention can be monitored according to any suitable method known in the art. For example, nuclear magnetic resonance, mass spectrometry, HPLC, and thin layer chromatography can be used to monitor the formation of product. The preparation of the compound may involve the protection and deprotection of multiple chemical groups. The necessity of protection and deprotection, as well as the selection of suitable protecting groups can be easily determined by those skilled in the art. The chemistry of protection groups is defined in Greene and Wuts, Protective Groups in Organic Synthesis, Third Edition, Wiley & Sons, 1999.

In a preferred embodiment of the present invention, the synthetic route of the compound according to the present invention is as follows:

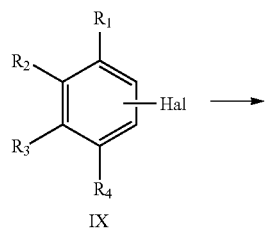

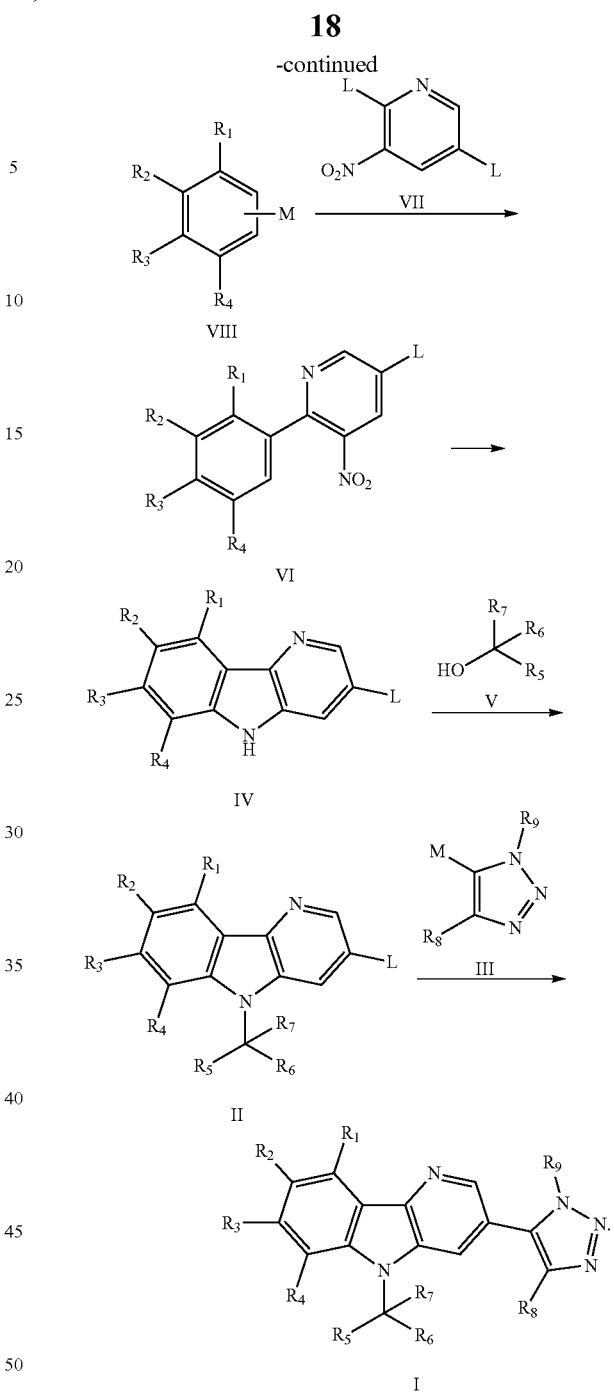

In general, the compounds of the present invention may be prepared by the reaction schemes and processes described above, but are not limited to the reagents and solvents in the reaction conditions. $R_1$, $R_2$, $R_3$, $R_4$, $R_5$, $R_6$, $R_7$, $R_8$, and $R_9$ are groups as defined above. Hal is halogen, which can easily be transferred into compound VIII. L is a leaving group, for example, halogen or OH can be transferred into a leaving group of trifluoromethanesulfonic acid. Suzuki reaction, for example, reacting 2,5-dibromo-3-nitropyridine and VII to provide pyridine compound VI. Next, reducing and ring closing with a phosphine reagent such as 1,2-bis(diphenylphosphino)ethane to give carboline compound IV. The nitrogen in the carboline compound IV can react with V under the Mitsunobu reaction conditions to give compound II. The carboline compound I is then obtained under suitable catalyst conditions with II and the intermediate compound III.

The technical features described above or in the Examples can be arbitrary combined. All of the features disclosed in the specification in this case may be used with any combination forms, the various features disclosed in the specification can be replaced by any alternative features which provides the same, equal or similar effects. Therefore, unless otherwise stated, the disclosed feature is only general examples of equal or similar features.

The advantages of the present invention are:
(1) The present invention provides a carboline derivative of novel structure;
(2) The compounds provided by the present invention have a significant inhibitory effect on the bromodomain;
(3) The present invention provides a pharmaceutical composition for the prevention or treatment of bromodomain-associated diseases.

The present invention will be further illustrated below with reference to the specific examples. It should be understood that these examples are only to illustrate the invention but not to limit the scope of the invention. The experimental methods with no specific conditions described in the following examples are generally performed under the conventional conditions such as J. Sambrook et al., Molecular Cloning: A Laboratory Manual (New York: Cold Spring Harbor Laboratory Press, 1989), or according to the manufacturer's instructions. Unless indicated otherwise, parts and percentage are calculated by weight.

Unless otherwise defined, the technical terms and scientific terminology used herein are of the same meanings as with that familiar to all to those skilled in the art. In addition, any methods and materials similar or equal to that recorded can be applied in the method described in the present invention. The preferred embodiments and the materials described herein are for demonstration purposes only.

Example 1

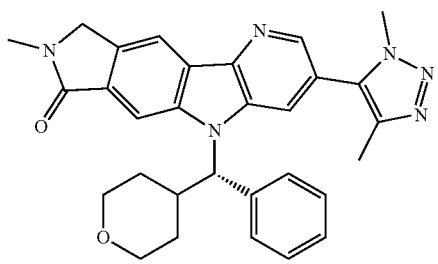

Compound 1

Step A

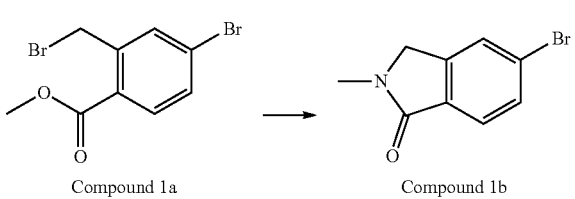

Compound 1a      Compound 1b

To a solution of compound 1a (15 g, 50 mmol) in methanol (150 ml) was added methylamine (25 ml, 33% in ethanol), and the reaction was refluxed overnight. After the organic solvent was drained off, the mixture was separated by silica gel column chromatography (PE/EA=3:1) to provide a yellow oily compound 1b.

HNMR (CDCl3), 7.5-7.7 (m, 3H), 4.3 (s, 2H), 3.1 (s, 3H). MS(ESI) m/z: 225.9 (M+H)+.

Step B

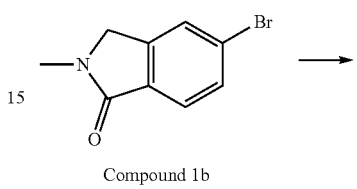

Compound 1b

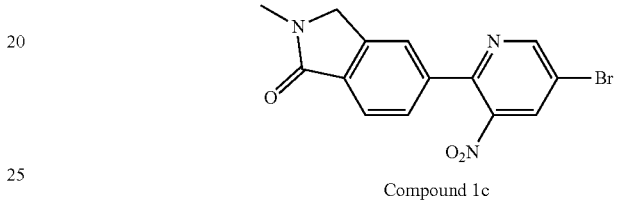

Compound 1c

To a mixed solution of compound 1b (5 g, 22 mmol), bisboronic acid pinacol (8.5 g, 33 mmol) and KOAc (3.2 g, 33 mmol) in 1,4 dioxane (50 ml) was added Pd(dppf)$_2$Cl$_2$ (1 g), and flushed with nitrogen. The reaction flask was sealed and the reaction was stirred overnight at 85° C. After cooling to room temperature, an aqueous Na$_2$CO$_3$ solution (2.5M, 10 ml), Pd(dppf)$_2$Cl$_2$ (1 g) and 2,5-dibromo-3-nitropyridine (9 g, 33 mmol) were added. After flushed with nitrogen for 10 minutes, the reaction flask was sealed and the mixture was stirred overnight at 85° C. The reaction was poured into water and extracted with ethyl acetate. The organic phase mixture was dried over Na$_2$SO$_4$, dried by suction and purified by silica gel column chromatography (PE:EA=10:1 to 1:1) to provide compound 1c as a yellow solid.

HNMR (CDCl3), 9.0 (s, 1H), 8.4 (s, 1H), 8.0 (d, 1H), 7.6-7.7 (m, 2H), 4.5 (s, 2H), 3.3 (s, 3H). MS(ESI) m/z:347.9 (M+H)+.

Step C

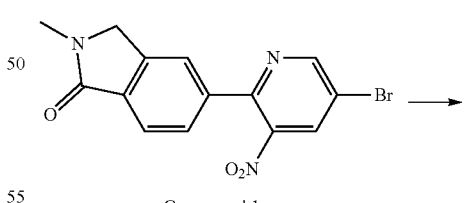

Compound 1c

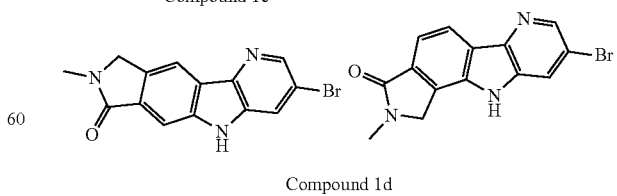

Compound 1d

Compound 1c (3.4 g, 10 mmol) was refluxed in triethylphosphite (50 ml) solution for 3 h. After the solvent was dried by suction, water was added. The solid obtained was washed and dried to provide a compound 1d mixture (of which the isomer ratio was approximately 6:4).

HNMR (DMSO), 11.8-12.2 (d, 1H), 8.6 (s, 1H), 8.2-8.4 (m, 2H), 7.4-7.8 (m, 1H), 4.4-4.8 (m, 2H), 3.0-3.4 (m, 3H). MS(ESI) m/z:316.0 (M+H)+.

Step D

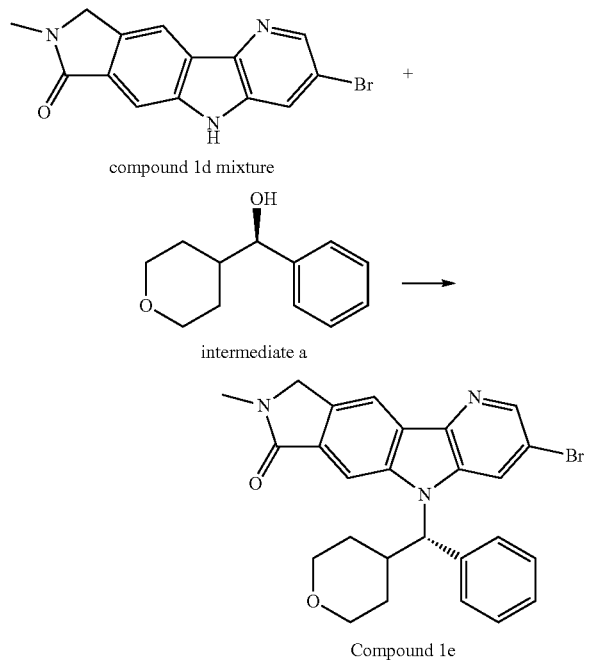 [SMILES: CN1Cc2cc3c(cc2C1=O)[nH]c1cc(Br)cnc13 ; O[C@@H](c1ccccc1)C1CCOCC1 ; CN1Cc2cc3c4ncc(Br)cc4n([C@H](c4ccccc4)C4CCOCC4)c3cc2C1=O]

The preparation of intermediate a referred to the method reported in literature [Orjales, A. et al. J. Med. Chem. 2003, 46, 5512-5532 and WO2015100282]. The compound 1d mixture (1.6 g, 5 mmol) was dissolved in DCM (35 ml), and PPh3 (2 g, 7.5 mmol) and intermediate a (0.7 g, 3.7 mmol) were added. The reaction mixture was stirred in ice-water bath for 1 h, then 10 ml of DIAD (1.5 g, 7.5 mmol) in DCM was slowly added dropwise, and then stirred at room temperature, TLC monitored until the reaction is complete. TLC test showed that only one isomer was consumed. After the solution was drained, the crude was purified by silica gel column chromatography (DCM:MeOH=50:1 to 10:1) to provide white compound 1e.

MS(ESI) m/z:490.0 (M+H)+.

Step E

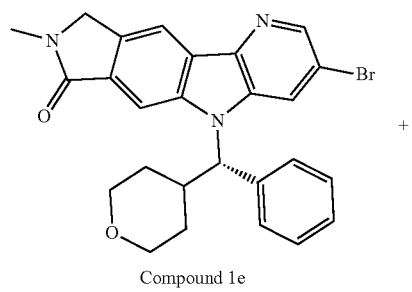

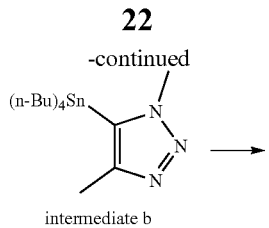

intermediate b

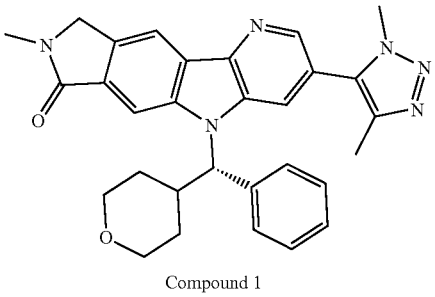

Compound 1

A mixed solution of compound 1e (500 mg, 1.02 mmol), intermediate b (592 mg, 1.5 mmol), triethylamine (0.3 ml, 2 mmol), Pd(dppf)$_2$Cl$_2$ (100 mg) in DMF (10 ml) was flushed with nitrogen. The reaction flask was sealed; the mixture was heated and stirred at 100-140° C. for 4 h, poured into water, and extracted with DCM. The combined organic phases were dried and aspirated to dryness to give crude product purified by silica gel column chromatography (DCM:MeOH=50:1 to 10:1) to provide crude product as a yellow solid and purified by HPLC to obtain compound 1.

HNMR (DMSO), 8.4-8.8 (m, 2H), 7.2-7.6 (m, 7H), 5.4-5.7 (m, 1H), 4.6 (s, 2H), 3.8-4.2 (m, 5H), 3.0-3.4 (m, 5H), 2.0-2.4 (m, 5H), 0.8-1.6 (m, 3H). MS(ESI) m/z: 507.2 (M+H)+.

Example 2

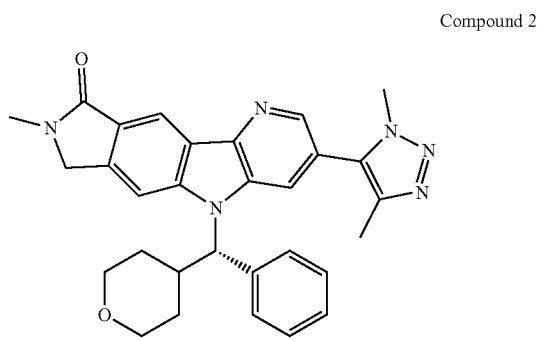 [SMILES: Cc1nnn(C)c1-c1cnc2c3cc4c(cc3n([C@H](c3ccccc3)C3CCOCC3)c2c1)CN(C)C4=O]

Compound 2

Step A

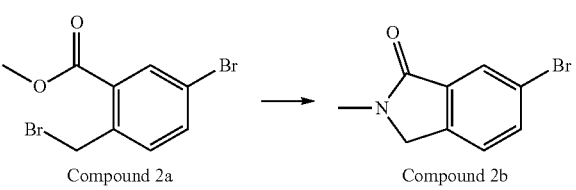

To a solution of compound 2a (15 g, 50 mmol) in methanol (150 ml) was added methylamine (25 ml, 33% in ethanol), and the reaction was refluxed overnight. After the organic solvent was drained off, the mixture was separated by silica gel column chromatography (PE/EA=3:1) to provide compound 2b as a yellow oily. MS(ESI) m/z:225.9 (M+H)+.

Step B

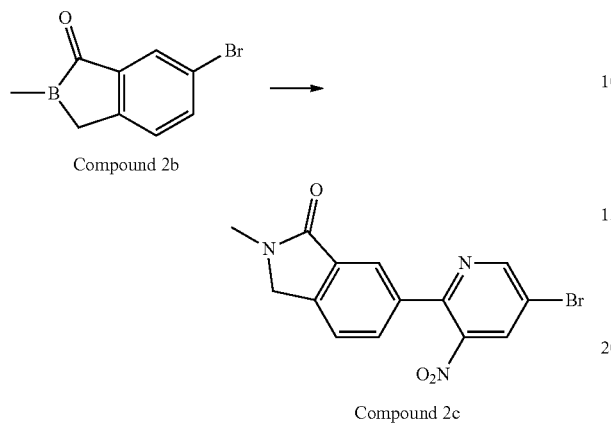

Compound 2b

Compound 2c

To a mixed solution of compound 2b (5 g, 22 mmol), bisboronic acid pinacol (8.5 g, 33 mmol) and KOAc (3.2 g, 33 mmol) in 1,4 dioxane (50 ml) was added Pd(dppf)$_2$Cl$_2$ (1 g), and flushed with nitrogen. The reaction flask was sealed and the reaction was stirred overnight at 85° C. After cooling to room temperature, an aqueous Na$_2$CO$_3$ solution (2.5M, 10 ml), Pd(dppf)$_2$Cl$_2$ (1 g) and 2,5-dibromo-3-nitropyridine (9 g, 33 mmol) were added. After flushed with nitrogen for 10 minutes, the reaction flask was sealed and the mixture was stirred overnight at 85° C. The reaction was poured into water and extracted with ethyl acetate. The organic phase mixture was dried over Na$_2$SO$_4$, dried by suction and purified by silica gel column chromatography (PE:EA=10:1 to 1:1) to provide compound 2c as a yellow solid.

HNMR (DMSO), 9.1 (s, 1H), 8.8 (s, 1H), 7.7-7.8 (m, 3H), 4.5 (s, 2H), 3.1 (s, 3H). MS(ESI) m/z: 347.9 (M+H)+.

Step C

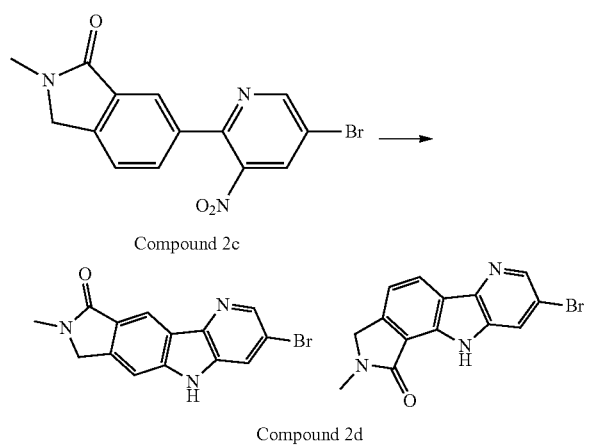

Compound 2c

Compound 2d

Compound 2c (3.4 g, 10 mmol) was refluxed in triethylphosphite (50 ml) solution for 3 h. After the solvent was drained, water was added. The solid obtained was washed and dried to provide a compound 2d mixture.

HNMR (DMSO), 11.8-12.2 (m, 1H), 8.0-8.6 (m, 3H), 7.2-7.8 (m, 1H), 4.4-4.6 (m, 2H), 3.0-3.1 (m, 3H). MS(ESI) m/z:316.0 (M+H)+.

Step D

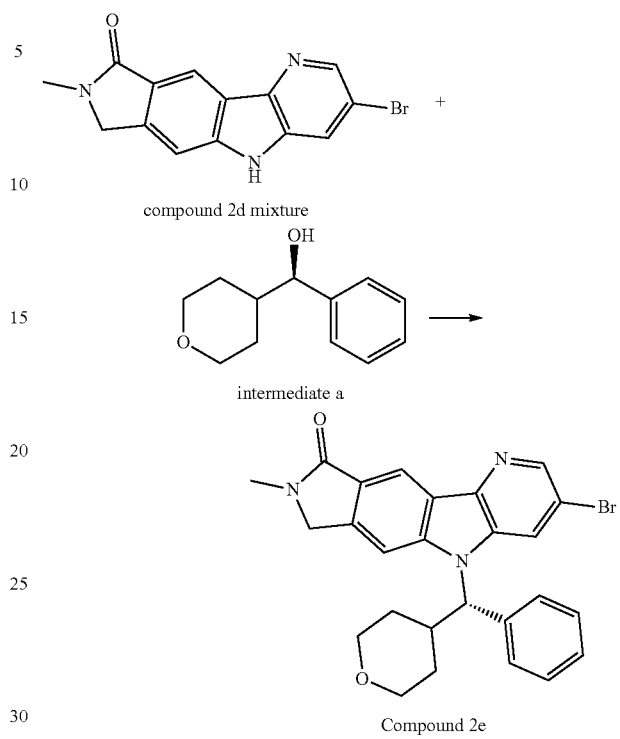

compound 2d mixture intermediate a

Compound 2e

The compound 2d mixture (1.6 g, 5 mmol) was dissolved in DCM (35 ml), and PPh3 (2 g, 7.5 mmol) and intermediate a (1.4 g, 7.5 mmol) were added. The reaction mixture was stirred in ice-water bath for 1 h, then 10 ml of DIAD (1.5 g, 7.5 mmol) in DCM was slowly added dropwise, and then stirred at room temperature, TLC monitored until the reaction is complete. TLC test showed that only one isomer was consumed. After the solution was drained, the crude was purified by silica gel column chromatography (DCM: MeOH=50:1 to 10:1) to provide white compound 2e.

MS(ESI) m/z:490.0 (M+H)+.

Step E

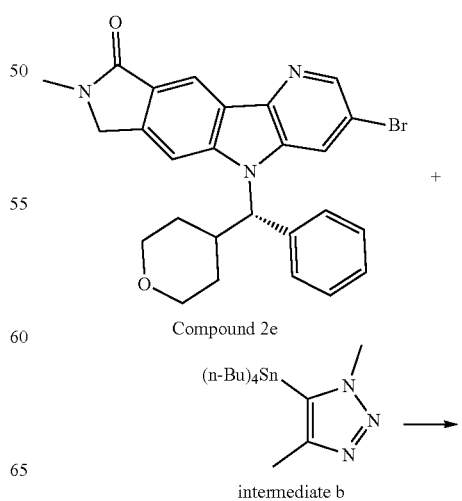

Compound 2e intermediate b

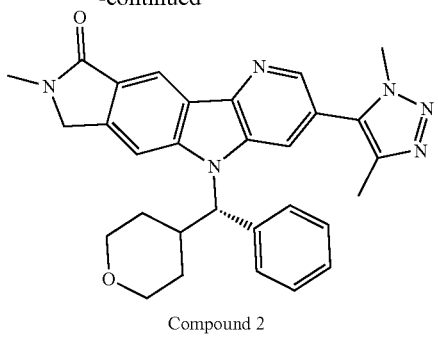

Compound 2

A mixture of compound 2e (500 mg, 1.02 mmol), intermediate b (592 mg, 1.5 mmol), triethylamine (0.3 ml, 2 mmol), and Pd(dppf)$_2$Cl$_2$ (100 mg) in DMF (10 ml) was flushed with nitrogen. The reaction flask was sealed; the mixture was heated and stirred at 100-140° C. for 4 h, poured into water, and extracted with DCM. The combined organic phases were dried and aspirated to dryness to give crude product purified by silica gel column chromatography (DCM:MeOH=50:1 to 10:1) to provide crude product as a yellow solid and purified by HPLC to obtain compound 2.

HNMR (DMSO), 8.9 (s, 1H), 8.6 (s, 1H), 7.7 (d, 2H), 7.2-7.5 (m, 5H), 5.6 (m, 1H), 4.6 (s, 2H), 3.8-4.2 (m, 5H), 3.0-3.6 (m, 5H), 2.0-2.4 (m, 5H), 1.0-1.6 (m, 3H). MS(ESI) m/z:507.2 (M+H)+.

Example 3

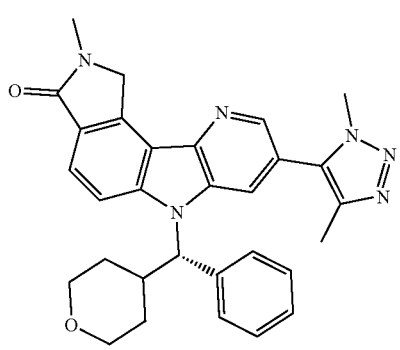

Compound 3

Step A

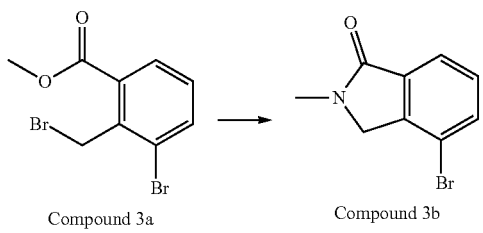

Compound 3a   Compound 3b

To a solution of compound 3a (15 g, 50 mmol) in methanol (150 ml) was added methylamine (25 ml, 33% in ethanol), and the reaction was refluxed overnight. After the organic solvent was drained off, the mixture was separated by silica gel column chromatography (PE/EA=3:1) to provide compound 3b as a yellow oily.

HNMR (DMSO) 7.7 (m, 1H), 7.6 (m, 2H), 4.4 (s, 2H), 3.0 (s, 3H). MS(ESI) m/z:225.9 (M+H)+.

Step B

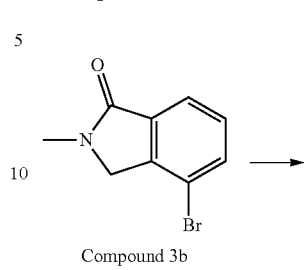

Compound 3b

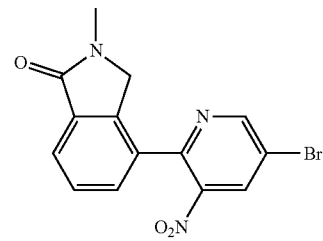

Compound 3c

To a mixed solution of compound 3b (5 g, 22 mmol), bisboronic acid pinacol (8.5 g, 33 mmol) and KOAc (3.2 g, 33 mmol) in 1,4-dioxane (50 ml) was added Pd(dppf)$_2$Cl$_2$ (1 g), and flushed with nitrogen. The reaction flask was sealed and the reaction was stirred overnight at 85° C. After cooled to room temperature, an aqueous Na$_2$CO$_3$ solution (2.5M, 10 ml), Pd(dppf)$_2$Cl$_2$ (1 g) and 2,5-dibromo-3-nitropyridine (9 g, 33 mmol) were added. After flushed with nitrogen for 10 minutes, the reaction flask was sealed and the mixture was stirred overnight at 85° C. The reaction was poured into water and extracted with ethyl acetate. The organic phase mixture was dried over Na$_2$SO$_4$, dried by suction and purified by silica gel column chromatography (PE:EA=10:2 to 1:1) to provide compound 3c as a yellow solid. MS(ESI) m/z:347.9 (M+H)+.

Step C

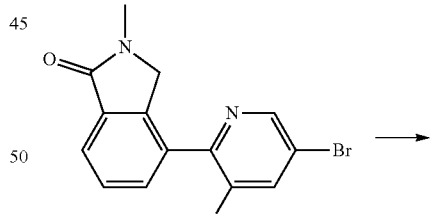

Compound 3c

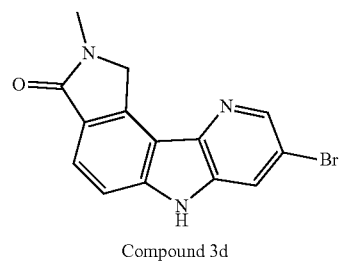

Compound 3d

Compound 3c (3.4 g, 10 mmol) was refluxed in triethylphosphite (50 ml) solution for 3 h. After the solvent was drained, water was added. The solid obtained was washed and dried to provide a compound 3d.

HNMR (DMSO), 11.8 (s, 1H), 8.5 (s, 1H), 8.1 (s, 1H), 7.7 (s, 1H), 7.6 (s, 1H), 4.7 (s, 2H), 3.1 (s, 3H). MS(ESI) m/z:316.0 (M+H)+.

Step D

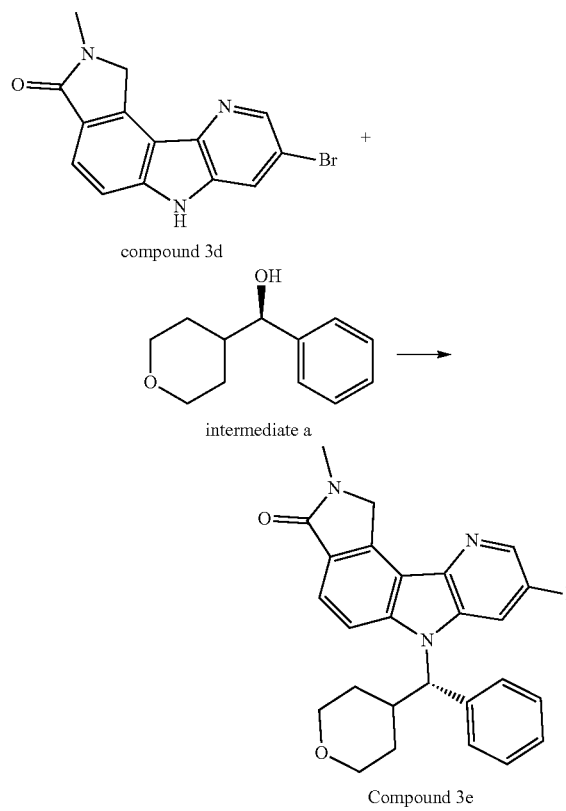

compound 3d intermediate a

Compound 3e

The compound 3d (1.6 g, 5 mmol) was dissolved in DCM (35 ml), and PPh3 (2 g, 7.5 mmol) and intermediate a (0.7 g, 3.7 mmol) were added. The reaction mixture was stirred in ice-water bath for 1 h, then a 10 ml solution of DIAD (1.5 g, 7.5 mmol) in DCM was slowly added dropwise, and then stirred at room temperature, TLC monitored until the reaction is completed. After the solution was dried by suction, the crude was purified by silica gel column chromatography (DCM:MeOH=50:1 to 10:1) to provide white compound 3e. MS(ESI) m/z: 490.0 (M+H)+.

Step E

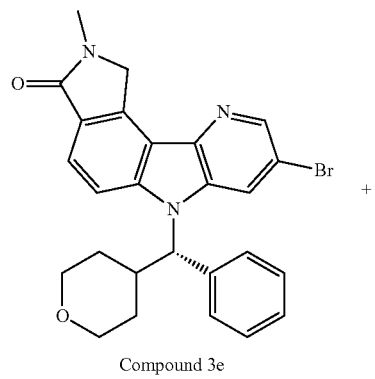

Compound 3e

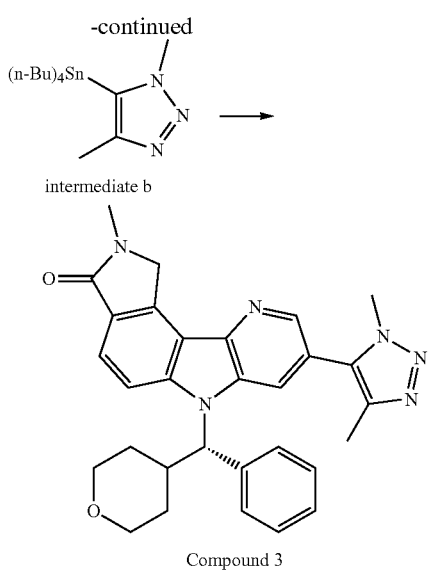

intermediate b

Compound 3

A mixture of compound 3e (500 mg, 1.02 mmol), intermediate b (592 mg, 1.5 mmol), triethylamine (0.3 ml, 2 mmol), Pd(dppf)$_2$Cl$_2$ (100 mg) in DMF (10 ml) was flushed with nitrogen. The reaction flask was sealed, the mixture was heated and stirred at 100-140° C. for 4 h, poured into water, and extracted with DCM. The combined organic phases were dried and aspirated to dryness to give crude product purified by silica gel column chromatography (DCM:MeOH=50:1 to 10:1) to provide crude product as a yellow solid purified by HPLC to obtain compound 3.

HNMR (DMSO), 8.6 (s, 1H), 8.1 (s, 1H), 7.7-7.9 (m, 2H), 7.2-7.5 (m, 5H), 5.6 (d, 1H), 5.0 (s, 2H), 3.8-4.1 (m, 5H), 3.0-3.8 (m, 5H), 2.0-2.4 (m, 5H), 1.0-1.8 (m, 3H). MS(ESI) m/z: 507.2 (M+H)+.

Example 4

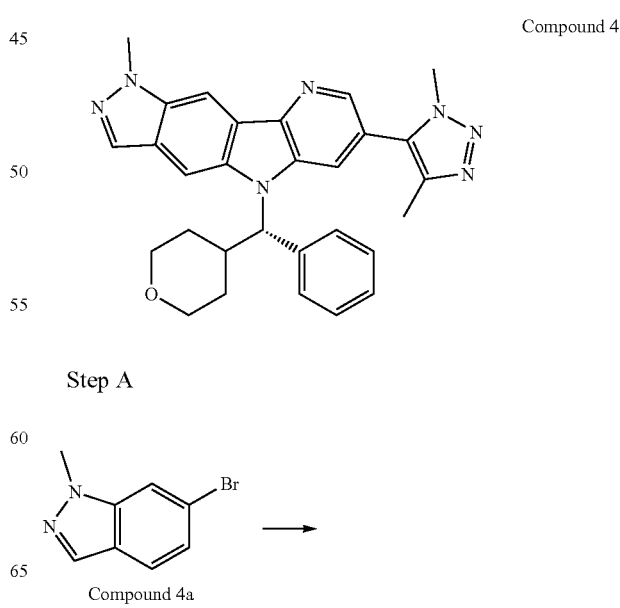

Compound 4

Step A

Compound 4a

-continued

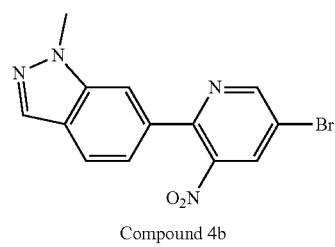
Compound 4b

To a mixed solution of compound 4a (10.5 g, 50 mmol), bisboronic acid pinacol (19 g, 75 mmol) and KOAc (7.5 g, 75 mmol) in 1,4-dioxane (150 ml) was added Pd(dppf)$_2$Cl$_2$ (1 g), and flushed with nitrogen. The reaction flask was sealed and the reaction was stirred overnight at 85° C. After cooling to room temperature, an aqueous Na$_2$CO$_3$ solution (2.5M, 30 ml), Pd(dppf)$_2$Cl$_2$ (1 g) and 2,5-dibromo-3-nitro-pyridine (21 g, 75 mmol) were added. After flushed with nitrogen for 10 minutes, the reaction flask was sealed and the mixture was stirred overnight at 85° C. The reaction was poured into water and extracted with ethyl acetate. The organic phase mixture was dried over Na$_2$SO$_4$, dried by suction and purified by silica gel column chromatography (PE:EA=10:1 to 1:1) to provide compound 4b as a yellow solid.

HNMR (CDCl3), 8.9 (s, 1H), 8.3 (s, 1H), 8.0 (s, 1H), 7.8 (m, 1H), 7.7 (m, 1H), 7.2 (m, 1H), 4.1 (s, 3H). MS(ESI) m/z: 332.8 (M+H)+.

Step B

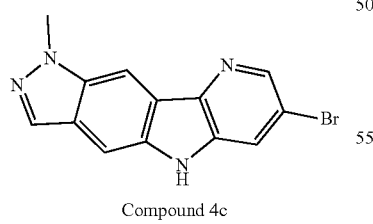
Compound 4b

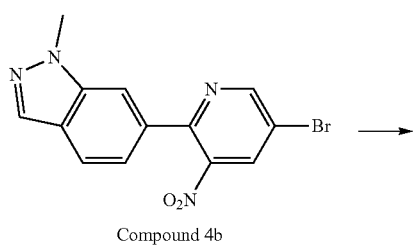
Compound 4c

Compound 4b (6.6 g, 20 mmol) was refluxed in triethyl-phosphite (80 ml) solution for 3 h. After the solvent was drained, water was added. The solid obtained was washed and dried to provide a compound 4c.

HNMR (CDCl3), 8.5 (s, 1H), 8.0-8.1 (m, 3H), 7.5 (s, 1H), 3.0 (s, 3H). MS(ESI) m/z:301.0 (M+H)+.

Step C

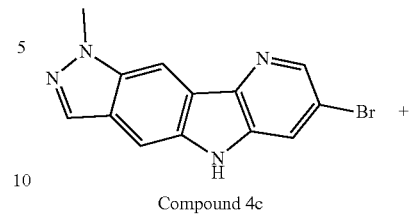
Compound 4c

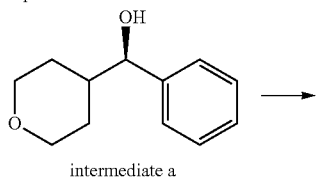
intermediate a

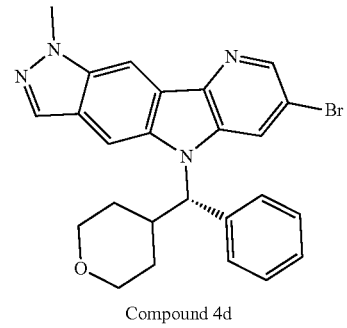
Compound 4d

Compound 4c (3 g, 10 mmol) was dissolved in DCM (250 ml), and PPh3 (4 g, 15 mmol) and intermediate a (2.9 g, 15 mmol) were added. The reaction mixture was stirred in ice-water bath for 1 h, then a 30 ml solution of DIAD (3 g, 15 mmol) in DCM was slowly added dropwise, and then stirred at room temperature, TLC monitored until the reaction is completed. After the solution was dried by suction, the crude was purified by silica gel column chromatography (DCM:MeOH=50:1 to 10:1) to provide white compound 4d.

HNMR (CDCl3), 8.6 (s, 1H), 8.2 (s, 1H), 8.0-8.1 (m, 1H), 7.8 (s, 1H), 7.6-7.7 (m, 2H), 7.3-7.6 (m, 4H), 6.0 (d, 1H), 4.4 (s, 3H), 3.9-4.0 (m, 1H), 3.6-3.7 (m, 1H), 3.4-3.5 (m, 1H), 3.1-3.2 (m, 1H), 2.8-3.0 (m, 1H), 2.0-2.1 (m, 1H), 0.8-1.4 (m, 2H), 0.5 (m, 1H). MS(ESI) m/z:475.0 (M+H)+.

Step D

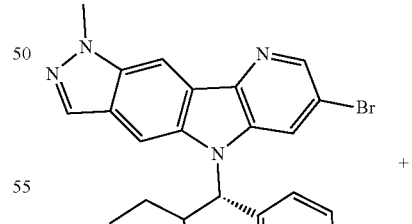
Compound 4d

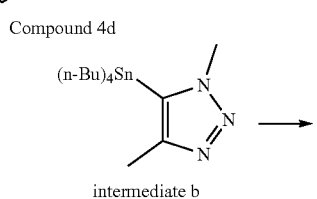
intermediate b

-continued

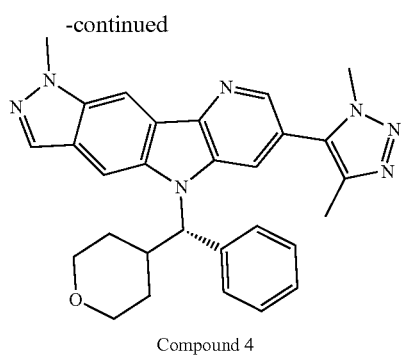

Compound 4

A mixed solution of compound 4d (1 g, 2.1 mmol), intermediate b (1.6 g, 4.2 mmol), triethylamine (0.6 ml, 4.2 mmol), Pd(dppf)$_2$Cl$_2$ (200 mg) in DMF (20 ml) was flushed with nitrogen. The reaction flask was sealed, the reaction was heated and stirred at 100-140° C. for 4 h, poured into water, and extracted with DCM. The combined organic phases were dried and aspirated to dryness to give crude product purified by silica gel column chromatography (DCM:MeOH=50:1 to 10:1) to provide crude product as a yellow solid purified by HPLC to obtain compound 4.

HNMR (CDCl3), 8.54 (s, 1H), 8.23 (s, 1H), 8.17 (d, 1H), 7.70 (d, 1H), 7.5 (m, 3H), 7.3-7.4 (m, 3H), 6.22 (d, 1H), 4.5 (s, 3H), 4.0 (m, 1H), 3.85 (s, 3H), 3.6-3.7 (m, 1H), 3.4-3.5 (m, 1H), 3.0-3.1 (m, 1H), 2.9-3.0 (m, 1H), 2.26 (s, 3H), 2.0-2.2 (m, 1H), 1.0-1.4 (m, 2H), 1.0 (m, 1H). MS(ESI) m/z:492.2 (M+H)+.

Example 5

Compound 5

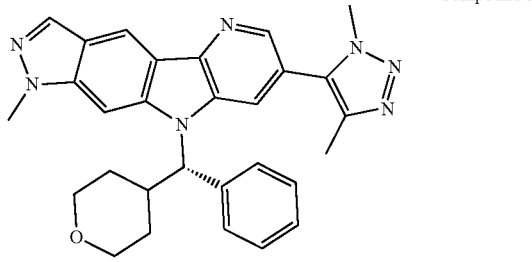

Step A

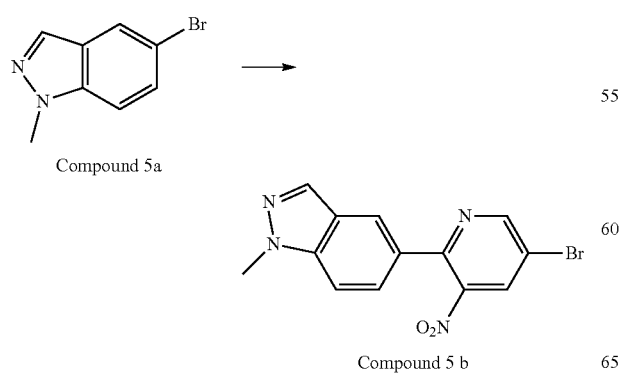

To a mixed solution of compound 5a (10.5 g, 50 mmol), bisboronic acid pinacol (19 g, 75 mmol) and KOAc (7.5 g, 75 mmol) in 1,4-dioxane (150 ml) was added Pd(dppf)$_2$Cl$_2$ (1 g), and flushed with nitrogen. The reaction flask was sealed and the reaction was stirred overnight at 85° C. After cooling to room temperature, an aqueous Na$_2$CO$_3$ solution (2.5M, 30 ml), Pd(dppf)$_2$Cl$_2$ (1 g) and 2,5-dibromo-3-nitro-pyridine (21 g, 75 mmol) were added. After flushed with nitrogen for 10 minutes, the reaction flask was sealed and the mixture was stirred overnight at 85° C. The reaction was poured into water and extracted with ethyl acetate. The mixed organic phase was dried over Na$_2$SO$_4$, dried by suction and purified by silica gel column chromatography (PE:EA=10:1 to 1:1) to provide compound 5b as a yellow solid.

HNMR (CDCl3), 8.9 (d, 1H), 8.3 (d, 1H), 8.0 (s, 1H), 7.9 (s, 1H), 7.5 (m, 1H), 7.4 (m, 1H), 4.1 (s, 3H). MS(ESI) m/z:332.8 (M+H)+.

Step B

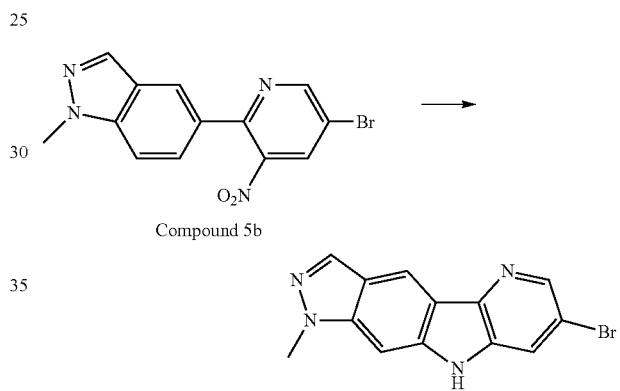

Compound 5b (6.6 g, 20 mmol) was refluxed in triethylphosphite (80 ml) solution for 3 h. After the solvent was drained, water was added. The solid obtained was washed and dried to provide a compound 5c.

HNMR (CDCl3), 8.5 (s, 1H), 8.25 (s, 1H), 8.18 (s, 1H), 7.88 (s, 1H), 7.2 (s, 1H), 4.1 (s, 3H). MS(ESI) m/z: 301.0 (M+H)+.

Step C

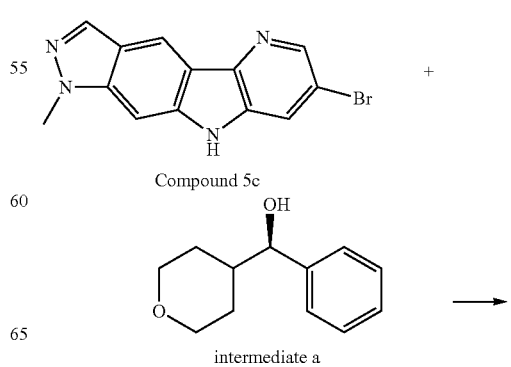

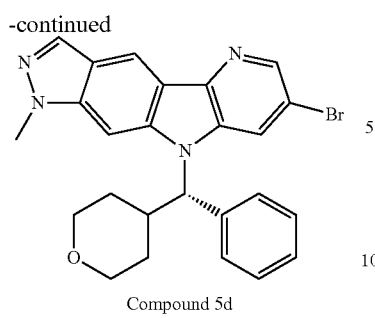

Compound 5d

Compound 5c (3 g, 10 mmol) was dissolved in DCM (200 ml), and PPh3 (4 g, 15 mmol) and intermediate a (2.9 g, 15 mmol) were added. The reaction mixture was stirred in ice-water bath for 1 h, and then a 30 ml solution of DIAD (3 g, 15 mmol) in DCM was slowly added dropwise, and then stirred at room temperature, TLC monitored until the reaction was completed. After the solution was dried by suction, the crude was purified by silica gel column chromatography (DCM:MeOH=50:1 to 10:1) to provide white compound 5d. MS(ESI) m/z:475.0 (M+H)+.

Step D

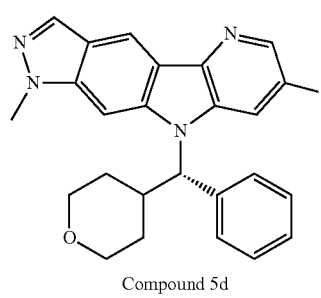

Compound 5d

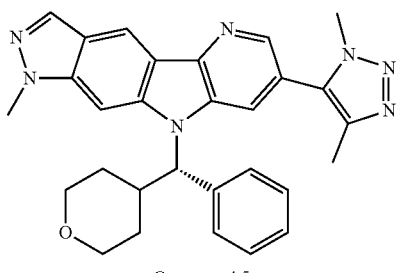

Compound 5

A mixed of compound 5d (1 g, 2.1 mmol), intermediate b (1.6 g, 4.2 mmol), triethylamine (0.6 ml, 4.2 mmol), Pd(dppf)$_2$Cl$_2$ (200 mg) in DMF (20 ml) was flushed with nitrogen. The reaction flask was sealed, the mixture was heated and stirred at 100-140° C. for 4 h, poured into water, and extracted with DCM. The combined organic phases were dried and aspirated to dryness to give crude product purified by silica gel column chromatography (DCM:MeOH=50:1 to 10:1) to provide crude product as a yellow solid purified by HPLC to obtain compound 5.

HNMR (DMSO), 9.0 (s, 1H), 8.52 (s, 1H), 8.27 (s, 1H), 8.2 (d, 1H), 7.5-7.7 (m, 3H), 7.2-7.4 (m, 3H), 6.0 (d, 1H), 4.3 (s, 3H), 4.1 (m, 1H), 3.95 (s, 3H), 3.0-3.8 (m, 4H), 2.26 (s, 3H), 1.8-2.0 (m, 1H), 1.0-1.4 (m, 3H). MS(ESI) m/z:492.2 (M+H)+.

Example 6

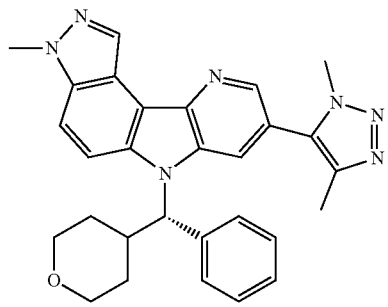

Compound 6

Step A

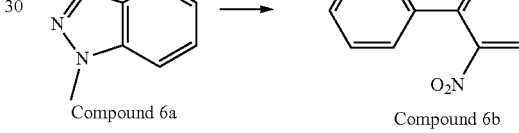

Compound 6a        Compound 6b

To a mixed solution of compound 6a (10.5 g, 50 mmol), bisboronic acid pinacol (19 g, 75 mmol) and KOAc (7.5 g, 75 mmol) in 1,4-dioxane (150 ml) was added Pd(dppf)$_2$Cl$_2$ (1 g), and flushed with nitrogen. The reaction flask was sealed and the reaction was stirred overnight at 85° C. After cooling to room temperature, an aqueous Na$_2$CO$_3$ solution (2.5M, 30 ml), Pd(dppf)$_2$Cl$_2$ (1 g) and 2,5-dibromo-3-nitropyridine (21 g, 75 mmol) were added. After flushed with nitrogen for 10 minutes, the reaction flask was sealed and the mixture was stirred overnight at 85° C. The reaction was poured into water and extracted with ethyl acetate. The mixed organic phase was dried over Na$_2$SO$_4$, dried by suction purified by silica gel column chromatography (PE:EA=10:1 to 1:1) to provide compound 6b as a yellow solid.

HNMR (CDCl3), 8.99 (s, 1H), 8.39 (s, 1H), 7.9 (s, 1H), 7.52 (m, 1H), 7.45 (m, 1H), 7.2 (m, 1H), 4.1 (s, 3H). MS(ESI) m/z:332.8 (M+H)+.

Step B

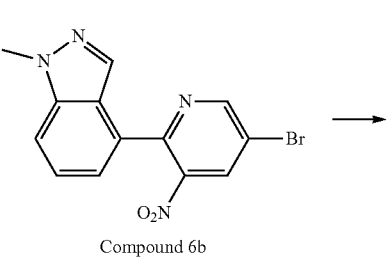

Compound 6b

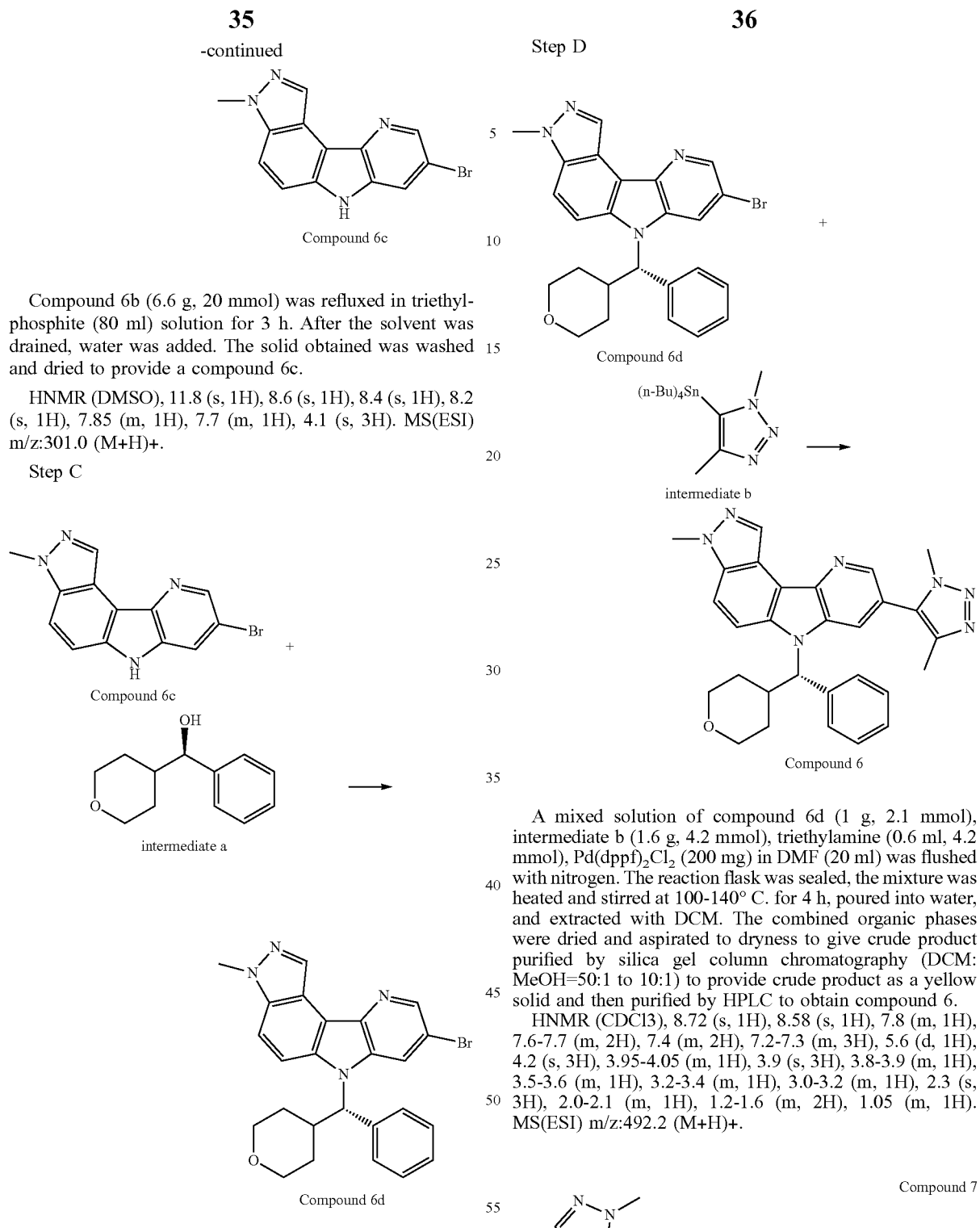

Compound 6b (6.6 g, 20 mmol) was refluxed in triethylphosphite (80 ml) solution for 3 h. After the solvent was drained, water was added. The solid obtained was washed and dried to provide a compound 6c.

HNMR (DMSO), 11.8 (s, 1H), 8.6 (s, 1H), 8.4 (s, 1H), 8.2 (s, 1H), 7.85 (m, 1H), 7.7 (m, 1H), 4.1 (s, 3H). MS(ESI) m/z:301.0 (M+H)+.

Step C

Compound 6c (3 g, 10 mmol) was dissolved in DCM (200 ml), and PPh3 (4 g, 15 mmol) and intermediate a (2.9 g, 15 mmol) were added. The reaction mixture was stirred in ice-water bath for 1 h, then a 30 ml solution of DIAD (3 g, 15 mmol) in DCM was slowly added dropwise, and then stirred at room temperature, TLC monitored until the reaction is completed. After the solution was dried by suction, the crude was purified by silica gel column chromatography (DCM:MeOH=50:1 to 10:1) to provide white compound 6d. MS(ESI) m/z:475.0 (M+H)+.

Step D

A mixed solution of compound 6d (1 g, 2.1 mmol), intermediate b (1.6 g, 4.2 mmol), triethylamine (0.6 ml, 4.2 mmol), Pd(dppf)$_2$Cl$_2$ (200 mg) in DMF (20 ml) was flushed with nitrogen. The reaction flask was sealed, the mixture was heated and stirred at 100-140° C. for 4 h, poured into water, and extracted with DCM. The combined organic phases were dried and aspirated to dryness to give crude product purified by silica gel column chromatography (DCM:MeOH=50:1 to 10:1) to provide crude product as a yellow solid and then purified by HPLC to obtain compound 6.

HNMR (CDCl3), 8.72 (s, 1H), 8.58 (s, 1H), 7.8 (m, 1H), 7.6-7.7 (m, 2H), 7.4 (m, 2H), 7.2-7.3 (m, 3H), 5.6 (d, 1H), 4.2 (s, 3H), 3.95-4.05 (m, 1H), 3.9 (s, 3H), 3.8-3.9 (m, 1H), 3.5-3.6 (m, 1H), 3.2-3.4 (m, 1H), 3.0-3.2 (m, 1H), 2.3 (s, 3H), 2.0-2.1 (m, 1H), 1.2-1.6 (m, 2H), 1.05 (m, 1H). MS(ESI) m/z:492.2 (M+H)+.

Example 7

Step A

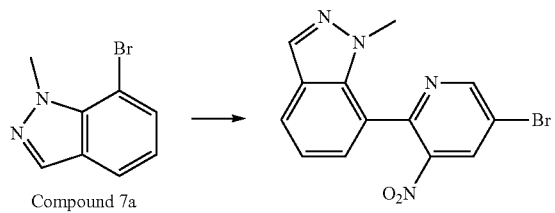

Compound 7a → Compound 7b

To a mixed solution of compound 7a (10.5 g, 50 mmol), bisboronic acid pinacol (19 g, 75 mmol) and KOAc (7.5 g, 75 mmol) in 1,4-dioxane (150 ml) was added Pd(dppf)$_2$Cl$_2$ (1 g), and flushed with nitrogen. The reaction flask was sealed and the reaction was stirred overnight at 85° C. After cooling to room temperature, an aqueous Na$_2$CO$_3$ solution (2.5M, 30 ml), Pd(dppf)$_2$Cl$_2$ (1 g) and 2,5-dibromo-3-nitropyridine (21 g, 75 mmol) were added. After flushed with nitrogen for 10 minutes, the reaction flask was sealed and the mixture was stirred overnight at 85° C. The reaction was poured into water and extracted with ethyl acetate. The mixed organic phase was dried over Na$_2$SO$_4$, dried by suction and purified by silica gel column chromatography (PE:EA=10:1 to 1:1) to provide compound 7b as a yellow solid.

HNMR (DMSO), 9.14 (s, 1H), 8.8 (s, 1H), 8.4 (s, 1H), 7.85 (m, 1H), 7.60 (m, 1H), 7.2 (m, 1H), 4.1 (s, 3H). MS(ESI) m/z:332.8 (M+H)+.

Step B

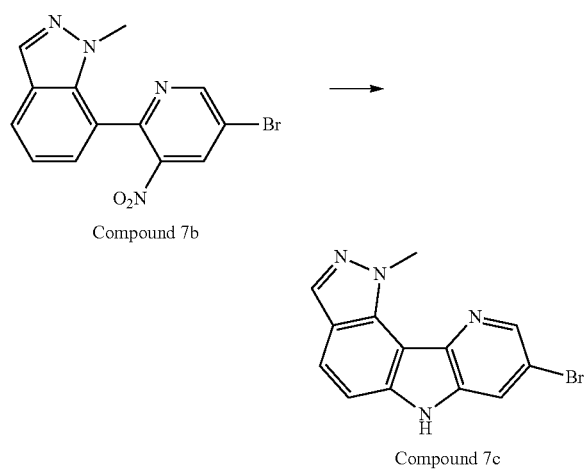

Compound 7b → Compound 7c

Compound 7b (6.6 g, 20 mmol) was refluxed in triethylphosphite (80 ml) solution for 3 h. After the solvent was drained, water was added. The solid obtained was washed and dried to provide a compound 7c.

HNMR (DMSO), 11.8 (s, 1H), 8.55 (s, 1H), 8.41 (s, 1H), 8.14 (s, 1H), 7.8 (m, 1H), 7.35 (m, 1H), 4.2 (s, 3H). MS(ESI) m/z:301.0 (M+H)+.

Step C

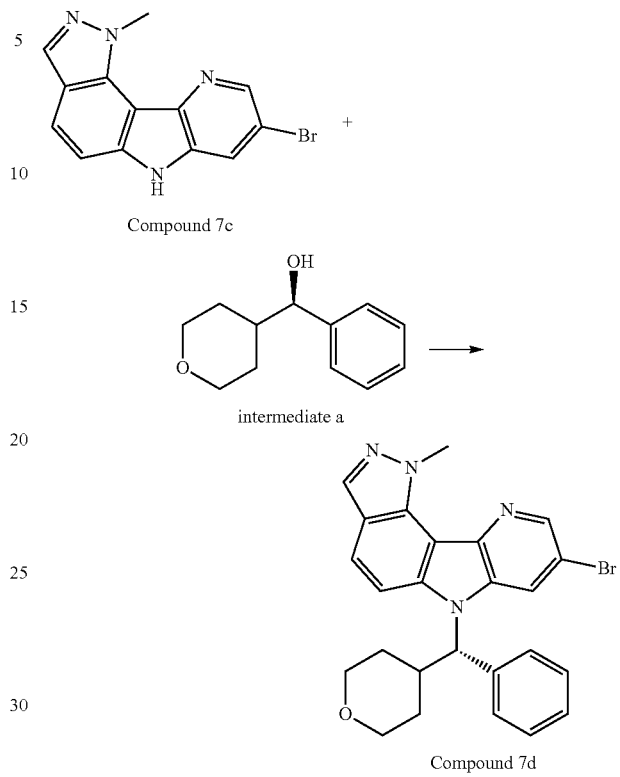

Compound 7c + intermediate a → Compound 7d

Compound 7c (3 g, 10 mmol) was dissolved in DCM (200 ml), and PPh3 (4 g, 15 mmol), intermediate a (2.9 g, 15 mmol) were added. The reaction mixture was stirred in ice-water bath for 1 h, and then 30 ml of DIAD (3 g, 15 mmol) in DCM was slowly added dropwise, and then stirred at room temperature, TLC monitored until the reaction is completed. After the solution was dried by suction, the crude was purified by silica gel column chromatography (DCM:MeOH=50:1 to 10:1) to provide white compound 7d.

HNMR (CDCl3), 8.6 (s, 1H), 8.1 (s, 1H), 7.8 (m, 1H), 7.4-7.5 (m, 3H), 7.2-7.4 (m, 4H), 5.5 (d, 1H), 4.9 (s, 3H), 4.0-4.1 (m, 1H), 3.8 (m, 1H), 3.5 (m, 1H), 3.3 (m, 1H), 3.1 (m, 1H), 2.0 (m, 1H), 1.8 (m, 1H), 1.2-1.4 (m, 1H), 0.8-1.0 (m, 1). MS(ESI) m/z:475.0 (M+H)+.

Step D

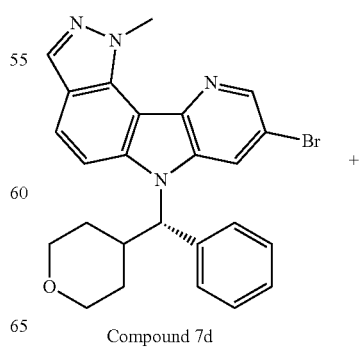

Compound 7d +

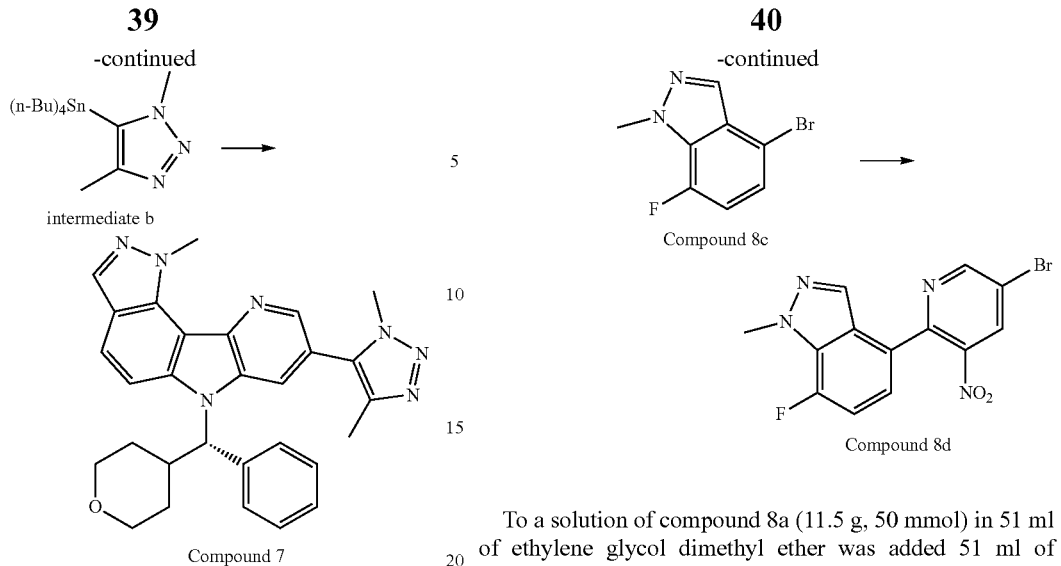

A mixed solution of compound 7d (1 g, 2.1 mmol), intermediate b (1.6 g, 4.2 mmol), triethylamine (0.6 ml, 4.2 mmol), and Pd(dppf)$_2$Cl$_2$ (200 mg) in DMF (20 ml) was flushed with nitrogen. The reaction flask was sealed; the mixture was heated and stirred at 100-140° C. for 4 h, poured into water, and extracted with DCM. The combined organic phases were dried and aspirated to dryness to give crude product purified by silica gel column chromatography (DCM:MeOH=50:1 to 10:1) to provide crude product as a yellow solid and purified by HPLC to obtain compound 7.

HNMR (DMSO), 8.62 (s, 1H), 8.15 (s, 1H), 7.89 (m, 2H), 7.68 (m, 2H), 7.2-7.4 (m, 4H), 5.93 (d, 1H), 4.9 (s, 3H), 4.0 (s, 3H), 3.0-4.0 (m, 5H), 2.31 (s, 3H), 1.0-2.0 (m, 4H). MS(ESI) m/z:492.2 (M+H)+.

Example 8

Compound 8

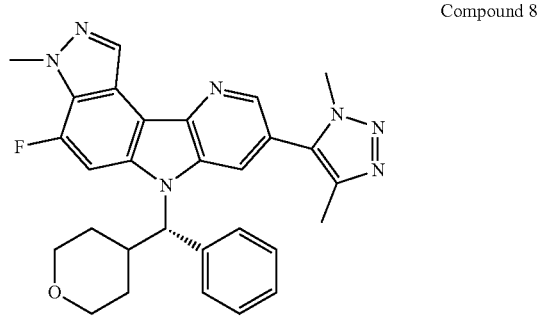 [SMILES: Cc1nnn(C)c1-c1cnc2c3c4cnn(C)c4c(F)cc3n([C@H](c3ccccc3)C3CCOCC3)c2c1]

Step A

To a solution of compound 8a (11.5 g, 50 mmol) in 51 ml of ethylene glycol dimethyl ether was added 51 ml of anhydrous hydrazine, and the reaction solution was stirred and refluxed for three hours. After cooled to room temperature, ethylene glycol dimethyl ether was distilled under reduced pressure. Ice was added to the residue to form a white solid. After filtrated and washed with water, the mixture was dissolved with dichloromethane and filtered. The filtrate was distilled under reduced pressure to provide compound 8b. MS (ESI) m/z: 215.2 (M+H)+.

To a solution of compound 8b (5.5 g, 25.6 mmol) in 100 ml of THF was added NaH (1.2 g, 30.7 mmol, 60%) in an ice bath. The reaction was stirred in an ice bath for one hour, and then 25 ml of THF solution containing CH3I (7.2 g, 51.2 mmol) was slowly added dropwise and then stirred overnight. The mixture was poured into water and extracted with ethyl acetate, and then the combined organic phases were dried, and dried by suction to obtain crude product which was purified by silica gel column chromatography (PE:EA=100:1 to 10:1) to give compound 8c as a white solid. MS (ESI) m/z: 229.2 (M+H)+.

To a mixed of compound 8c (11 g, 48 mmol), bisboronic acid pinacol (14.4 g, 56.8 mmol) and KOAc (9.3 g, 95 mmol) in 1,4-dioxane (200 ml) was added Pd(dppf)$_2$Cl$_2$ (1.5 g), and flushed with nitrogen. The reaction flask was sealed and the reaction was stirred overnight at 85° C. After cooled to room temperature, an aqueous Na$_2$CO$_3$ solution (2.5M, 38 ml), Pd(dppf)$_2$Cl$_2$ (1 g) and 2,5-dibromo-3-nitropyridine (16 g, 56.8 mmol) were added. After flushed with nitrogen for 10 minutes, the reaction flask was sealed and the mixture was stirred overnight at 85° C. The reaction was poured into water and extracted with ethyl acetate. The mixed organic phase was dried over Na$_2$SO$_4$, dried by suction and purified by silica gel column chromatography (PE:EA=10:1 to 1:1) to provide compound 8d as a yellow solid. MS(ESI) m/z: 351.2 (M+H)+.

Step B

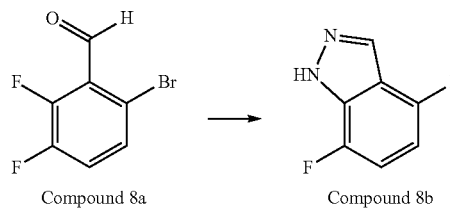

Compound 8a    Compound 8b

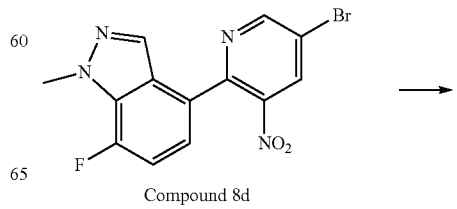

Compound 8d

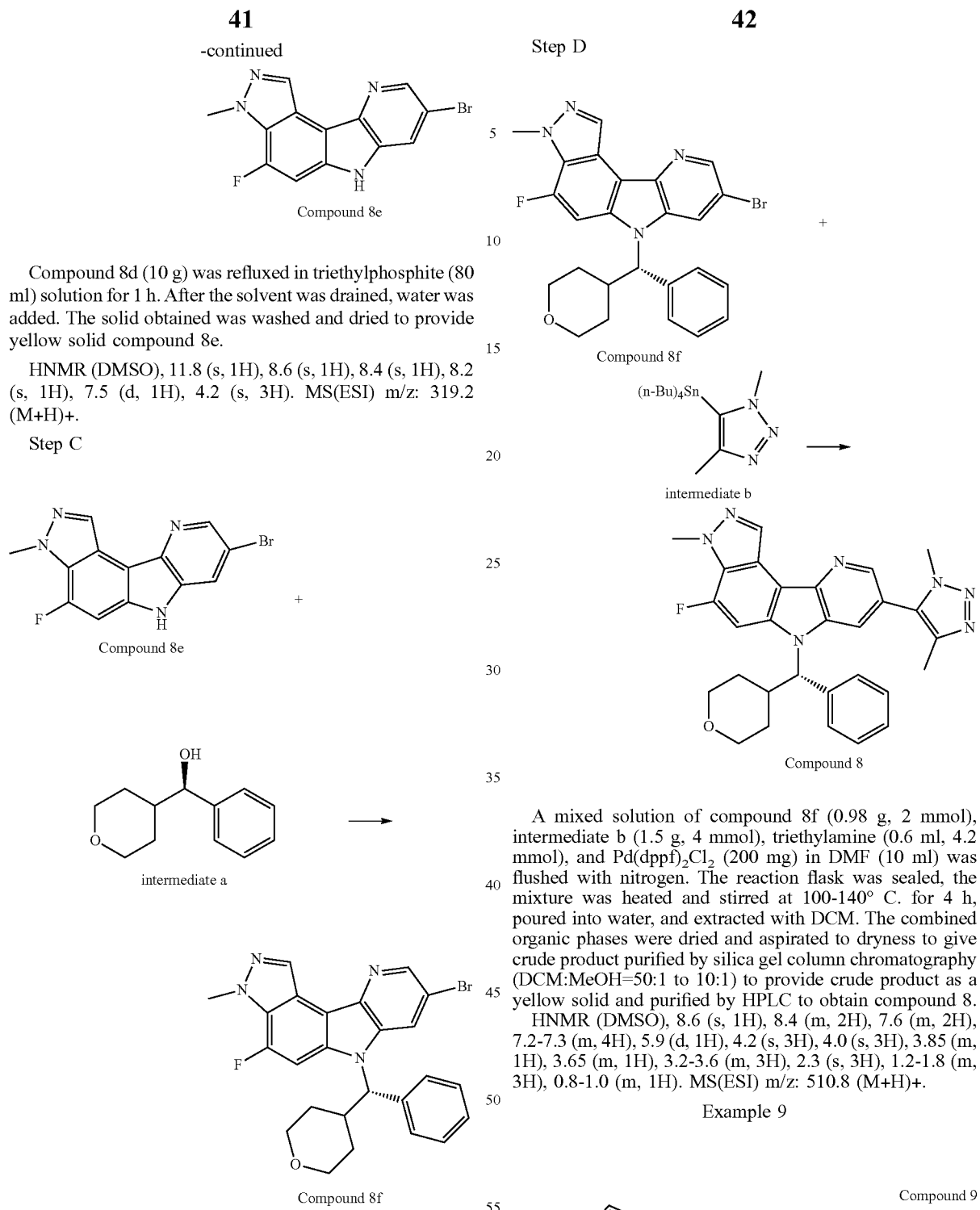

Compound 8d (10 g) was refluxed in triethylphosphite (80 ml) solution for 1 h. After the solvent was drained, water was added. The solid obtained was washed and dried to provide yellow solid compound 8e.

HNMR (DMSO), 11.8 (s, 1H), 8.6 (s, 1H), 8.4 (s, 1H), 8.2 (s, 1H), 7.5 (d, 1H), 4.2 (s, 3H). MS(ESI) m/z: 319.2 (M+H)+.

Step C

Compound 8e (2 g, 6.3 mmol) was dissolved in DCM (40 ml), and PPh3 (3.3 g, 12.6 mmol) and intermediate a (2.4 g, 12.6 mmol) were added. The reaction mixture was stirred in ice-water bath for 1 h, then a 10 ml solution of DIAD (3 g, 15 mmol) in DCM was slowly added dropwise, and then stirred at room temperature for 2 days, TLC monitored until the reaction was completed. After the solution was dried by suction, the crude was purified by silica gel column chromatography (DCM:MeOH=50:1 to 10:1) to provide compound 8f as a yellow solid. MS(ESI) m/z:493.4 (M+H)+.

Step D

A mixed solution of compound 8f (0.98 g, 2 mmol), intermediate b (1.5 g, 4 mmol), triethylamine (0.6 ml, 4.2 mmol), and Pd(dppf)$_2$Cl$_2$ (200 mg) in DMF (10 ml) was flushed with nitrogen. The reaction flask was sealed, the mixture was heated and stirred at 100-140° C. for 4 h, poured into water, and extracted with DCM. The combined organic phases were dried and aspirated to dryness to give crude product purified by silica gel column chromatography (DCM:MeOH=50:1 to 10:1) to provide crude product as a yellow solid and purified by HPLC to obtain compound 8.

HNMR (DMSO), 8.6 (s, 1H), 8.4 (m, 2H), 7.6 (m, 2H), 7.2-7.3 (m, 4H), 5.9 (d, 1H), 4.2 (s, 3H), 4.0 (s, 3H), 3.85 (m, 1H), 3.65 (m, 1H), 3.2-3.6 (m, 3H), 2.3 (s, 3H), 1.2-1.8 (m, 3H), 0.8-1.0 (m, 1H). MS(ESI) m/z: 510.8 (M+H)+.

Example 9

Step A

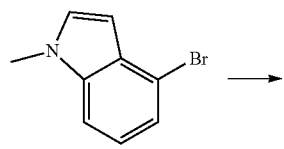

Compound 9a

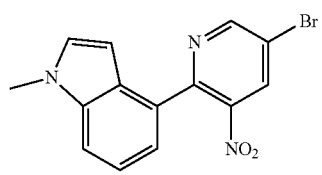

Compound 9b

To a mixed solution of compound 9a (5 g, 24 mmol), bisboronic acid pinacol (7.6 g, 30 mmol) and KOAc (5 g, 48 mmol) in 1,4-dioxane (150 ml) was added Pd(dppf)$_2$Cl$_2$ (1 g), and flushed with nitrogen. The reaction flask was sealed and the reaction was stirred overnight at 85° C. After cooling to room temperature, an aqueous Na$_2$CO$_3$ solution (2.5M, 20 ml), Pd(dppf)$_2$Cl$_2$ (1 g) and 2,5-dibromo-3-nitropyridine (8 g, 30 mmol) were added. After flushed with nitrogen for 10 minutes, the reaction flask was sealed and the mixture was stirred overnight at 85° C. The reaction was poured into water and extracted with ethyl acetate. The mixed organic phase was dried over Na$_2$SO$_4$, dried by suction and purified by silica gel column chromatography (PE:EA=10:1 to 1:1) to provide compound 9b as a yellow solid.

HNMR (DMSO), 9.0 (s, 1H), 8.8 (s, 1H), 7.5 (m, 1H), 7.4 (m, 1H), 7.2-7.3 (m, 2H), 7.1-7.2 (m, 1H), 3.8 (s, 3H). MS(ESI) m/z:332.4 (M+H)+.

Step B

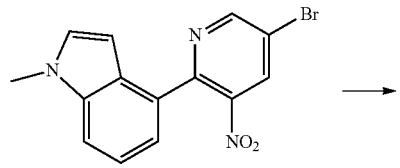

Compound 9b

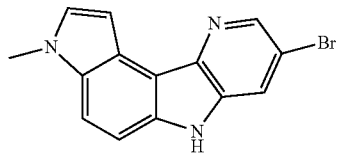

Compound 9c

Compound 9b (5 g, 15 mmol) was refluxed in triethylphosphite (50 ml) solution for 1 h. After the solvent was drained, water was added. The solid obtained was washed and dried to provide a compound 9c.

HNMR (DMSO), 11.5 (s, 1H), 8.5 (s, 1H), 8.1 (s, 1H), 7.7 (m, 1H), 7.47 (s, 1H), 7.4 (m, 1H), 7.0 (s, 1H), 3.9 (s, 3H). MS(ESI) m/z:301.2 (M+H)+.

Step C

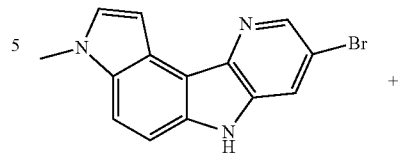

Compound 9c

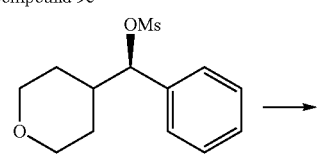

intermediate c

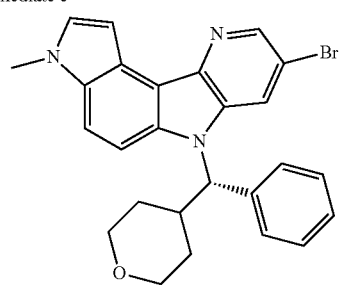

Compound 9d

Compound 9c (2 g, 6.6 mmol) was dissolved in dry DMF (30 ml), and Cs$_2$CO$_3$ (5 g, 14.4 mmol) and intermediate c (3.2 g, 13.2 mmol) were added. The reaction mixture was stirred at 45° C. for three days and then intermediate c (3.2 g, 13.2 mmol) was added dropwise, and stirred at 50° C. for three days. After the solution was drained, the crude product was purified by column chromatography on silica gel (DCM:MeOH=50:1 to 10:1) to obtain yellow compound 9d.

HNMR (CD3Cl), 8.55 (s, 1H), 7.96 (s, 1H), 7.2-7.6 (m, 9H), 5.4 (d, 1H), 3.7-4.0 (m, 5H), 3.0-3.4 (m, 3H), 1.0-2.0 (m, 4H). MS(ESI) m/z:474.2.0 (M+H)+.

Step D

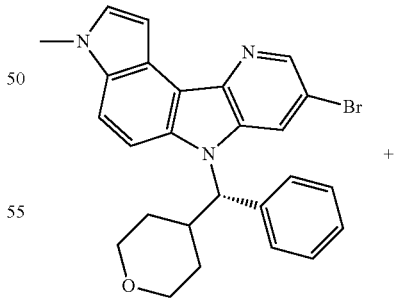

Compound 9d

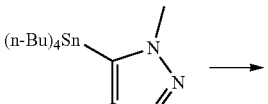

intermediate b

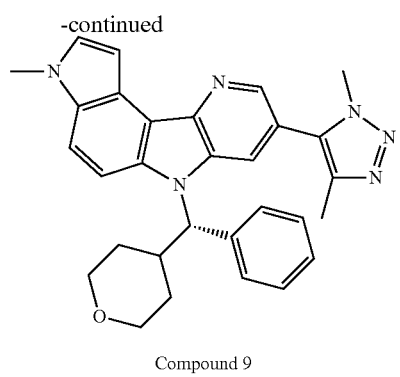

Compound 9

A mixed solution of compound 9d (0.8 g, 1.7 mmol), intermediate b (1.3 g, 3.4 mmol), triethylamine (0.6 ml, 4.2 mmol), and Pd(dppf)$_2$Cl$_2$ (200 mg) in DMF (10 ml) was flushed with nitrogen. The reaction flask was sealed, the mixture was heated and stirred at 100-140° C. for 4 h, poured into water, and extracted with DCM. The combined organic phases were dried and aspirated to dryness to give crude product purified by silica gel column chromatography (DCM:MeOH=50:1 to 10:1) to provide crude product as a yellow solid and purified by HPLC to obtain compound 9.

HNMR (CDCl3), 8.88 (s, 1H), 8.59 (s, 1H), 7.8-7.9 (m, 2H), 7.7 (s, 1H), 7.2-7.6 (m, 6H), 5.6 (d, 1H), 4.1 (m, 1H), 3.9 (s, 3H), 3.8 (m, 1H), 3.5 (m, 1H), 3.3 (m, 1H), 3.1 (m, 1H), 2.3 (s, 3H), 2.0 (m, 4H), 1.4 (m, 1H), 1.2 (m, 1H), 1.05 (m, 1H). MS(ESI) m/z:491.8 (M+H)+.

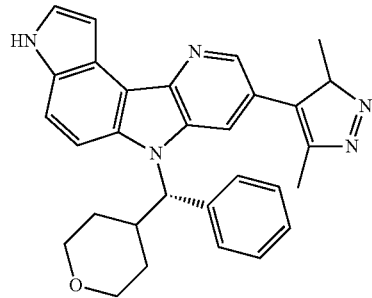

Compound 10

Example 10

Step A

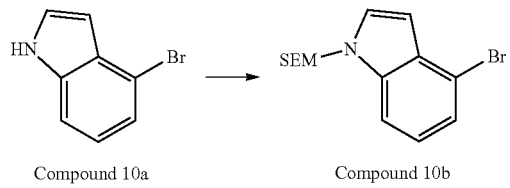 [SMILES: Brc1cccc2[nH]ccc12 ; C[Si](C)(C)CCOCn1ccc2c(Br)cccc21]

Compound 10a    Compound 10b

To a solution of compound 10a (10 g, 51 mmol) in 100 ml of THF was added NaH (2.4 g, 60 mmol, 60%) in an ice bath. The reaction was stirred in an ice bath for one hour, and then 25 ml of THF solution containing 2-(trimethylsilyl) ethoxymethyl chloride (SEMCl, 8.5 g, 51.2 mmol) was slowly added dropwise and then stirred overnight. The mixture was poured into water and extracted with ethyl acetate, and then the combined organic phases were dried, and dried by sunction to obtain a crude product purified by a silica gel column chromatography (PE:EA=100:1 to 10:1) to give compound 10b as a white solid.

HNMR (CDCl3), 7.4 (m, 1H), 7.3 (m, 1H), 7.2 (m, 1H), 7.05 (m, 1H), 6.5 (m, 1H), 5.4 (s, 2H), 3.4 (m, 2H), 0.9 (m, 2H), 0 (m, 9H). MS(ESI) m/z:326.2 (M+H)+.

Step B

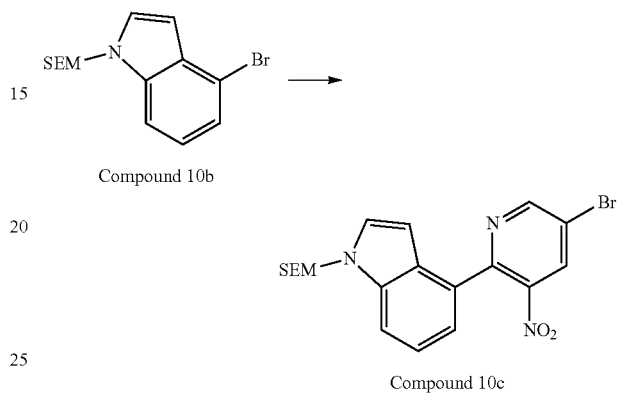

Compound 10b

Compound 10c

To a mixed solution of compound 1b (15 g, 46 mmol), bisboronic acid pinacol (14.4 g, 56.8 mmol) and KOAc (9.3 g, 95 mmol) in 1,4-dioxane (200 ml) was added Pd(dppf)$_2$Cl$_2$ (1.5 g), and flushed with nitrogen. The reaction flask was sealed and the reaction was stirred overnight at 85° C. After cooling to room temperature, aqueous Na$_2$CO$_3$ solution (2.5M, 38 ml), Pd(dppf)$_2$Cl$_2$ (1 g) and 2,5-dibromo-3-nitro-pyridine (16 g, 56.8 mmol) were added. After flushed with nitrogen for 10 minutes, the reaction flask was sealed and the mixture was stirred overnight at 85° C. The reaction was poured into water and extracted with ethyl acetate. The mixed organic phase was dried over Na$_2$SO$_4$, dried by suction and purified by silica gel column chromatography (PE:EA=10:1 to 1:1) to provide compound 10c as a yellow solid.

HNMR (CDCl3), 8.96 (s, 1H), 8.39 (s, 1H), 7.6 (m, 1H), 7.2-7.3 (m, 3H), 6.4 (m, 1H), 5.5 (s, 2H), 3.4-3.5 (m, 2H), 0.8-0.9 (m, 2H), 0 (m, 9H). MS (ESI) m/z: 448.2 (M+H)+.

Step C

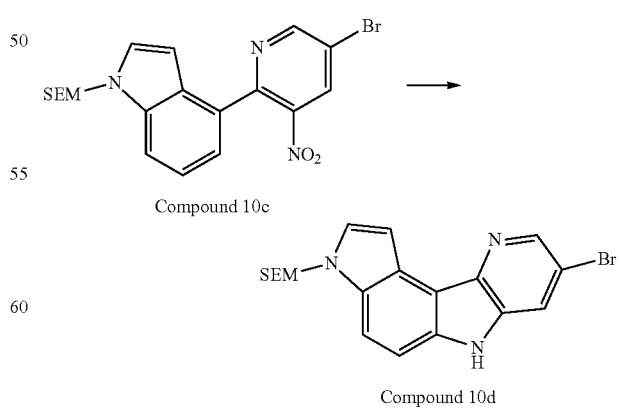

Compound 10c

Compound 10d

Compound 10c (12.5 g, 30 mmol) in triethyl phosphite (150 ml) was refluxed for 1 h, and then stirred in an ice bath to give a solid, which was filtered, washed with water and diethyl ether, and dried to give compound 10d.

HNMR (DMSO), 11.6 (s, 1H), 8.6 (s, 1H), 8.2 (s, 1H), 7.9 (m, 1H), 7.7 (s, 1H), 7.5 (m, 1H), 7.2 (s, 1H), 5.77 (s, 2H), 3.4-3.5 (m, 2H), 0.8-1.0 (m, 2H), 0 (s, 9H). MS (ESI) m/z: 416.2 (M+H)+.

Step D

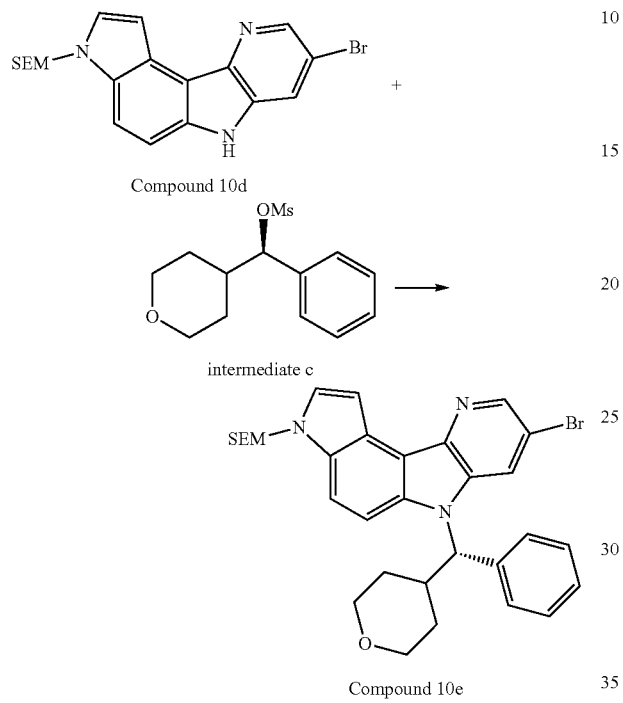

Compound 10d (3 g, 7.2 mmol) was dissolved in dry DMF (30 ml), and Cs$_2$CO$_3$ (5 g, 14.4 mmol) and intermediate c (3.8 g, 14.4 mmol) were added. The reaction mixture was stirred at 45° C. for three days and then intermediate c (2 g, 8 mmol) was added dropwise, and stirred at 50° C. for three days. After the solution was drained, the crude product was purified by column chromatography on silica gel (DCM:MeOH=50:1 to 10:1) to obtain yellow compound 10e.

HNMR (CDCl3), 8.6 (s, 1H), 8.0 (s, 1H), 7.7 (m, 1H), 7.5 (m, 3H), 7.2-7.4 (m, 5H), 5.6 (s, 2H), 5.5 (d, 1H), 3.0-4.0 (m, 8H), 1.0-2.0 (m, 4H), 0.9 (m, 2H), 0 (m, 9H). MS(ESI) m/z:590.2 (M+H)+.

Step E

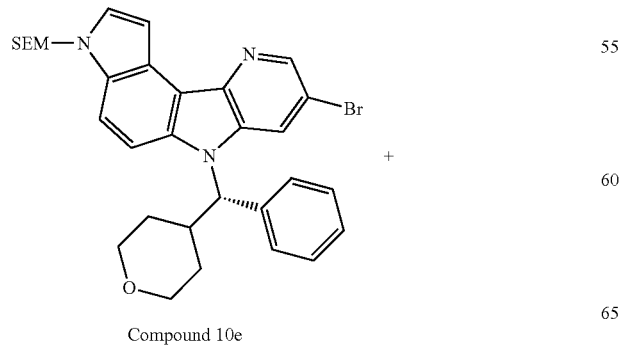

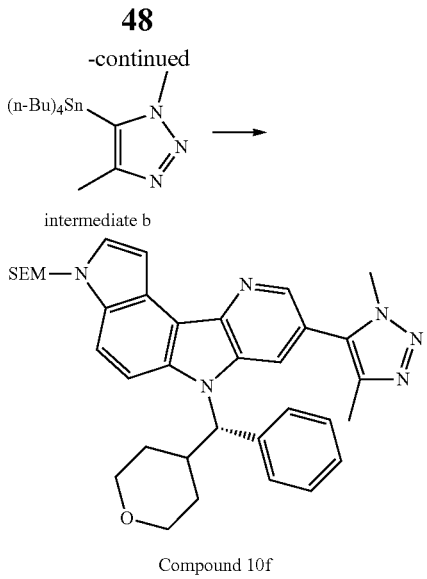

A mixed solution of compound 10e (1.5 g, 2.5 mmol), intermediate b (2 g, 5 mmol), triethylamine (0.7 ml, 5 mmol), Pd(dppf)$_2$Cl$_2$ (300 mg) in DMF (20 ml) was flushed with nitrogen. The reaction flask was sealed, the mixture was heated and stirred at 100-140° C. for 4 h, poured into water, and extracted with DCM. The combined organic phases were dried and aspirated to dryness to give crude product purified by silica gel column chromatography (DCM:MeOH=50:1 to 10:1) to provide crude product 10f as a yellow solid. MS(ESI) m/z:607.2 (M+H)+.

Step F

A mixed solution of compound 10f (300 mg, 0.5 mmol) and TBAF (2 ml, 1.0 M in THF) in THF (5 ml) was heated under reflux and stirred for 18 h. The crude product was obtained by aspirate and purified by silica gel column chromatography (DCM:MeOH=50:1 to 10:1) to obtain crude yellow solid which was purified by HPLC to give compound 10.

HNMR (CDCl3), 9.39 (s, 1H), 8.62 (s, 1H), 7.8 (m, 1H), 7.7 (m, 1H), 7.6 (m, 1H), 7.2-7.6 (m, 6H), 5.6 (d, 1H), 4.14 (m, 1H), 3.8-4.0 (m, 4H), 3.5-3.7 (m, 1H), 3.3-3.5 (m, 1H), 3.1-3.3 (m, 1H), 2.3 (s, 3H), 2.0-2.2 (m, 1H), 1.6-1.8 (m, 1H), 1.4-1.6 (m, 1H), 1.1-1.3 (m, 1H).

MS(ESI) m/z: 477.4 (M+H)+.

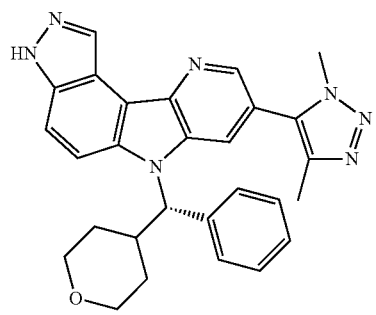

Compound 11

Example 11

Step A

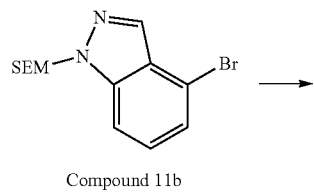

Compound 11a    Compound 11b

To a solution of compound 11a (10 g, 51 mmol) in 100 ml of THF was added NaH (2.4 g, 60 mmol, 60%) in an ice bath. The reaction was stirred in an ice bath for one hour, and then 25 ml of THF solution containing 2-(trimethylsilyl)ethoxymethyl chloride (SEMCl, 8.5 g, 51.2 mmol) was slowly added dropwise and then stirred overnight. The mixture was poured into water and extracted with ethyl acetate, and then the combined organic phases were dried, and dired by suction to obtain a crude product purified by silica gel column chromatography (PE:EA=100:1 to 10:1) to give compound 11b as a white solid.

HNMR (CDCl3), 8.0 (m, 1H), 7.5 (m, 1H), 7.2-7.4 (m, 2H), 5.7 (m, 2H), 3.5 (m, 2H), 0.9 (m, 2H), 0 (m, 9H). MS(ESI) m/z:327.2 (M+H)+.

Step B

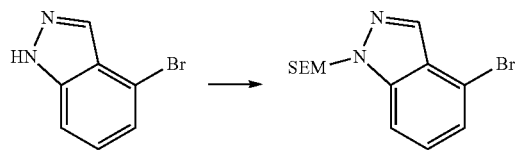

Compound 11b

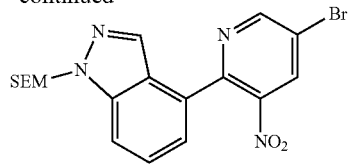

Compound 11c

To a mixed solution of compound 11b (15 g, 46 mmol), bisboronic acid pinacol (14.4 g, 56.8 mmol) and KOAc (9.3 g, 95 mmol) in 1,4-dioxane (200 ml) was added Pd(dppf)2Cl2 (1.5 g), and flushed with nitrogen. The reaction flask was sealed and the reaction was stirred overnight at 85° C. After cooling to room temperature, aqueous Na2CO3 solution (2.5M, 38 ml), Pd(dppf)2Cl2 (1 g) and 2,5-dibromo-3-nitropyridine (16 g, 56.8 mmol) were added. After flushed with nitrogen for 10 minutes, the reaction flask was sealed and the mixture was stirred overnight at 85° C. The reaction was poured into water and extracted with ethyl acetate. The mixed organic phase was dried over Na2SO4, dried by suction and purified by silica gel column chromatography (PE:EA=10:1 to 1:1) to provide compound 11c as a yellow solid.

HNMR (CDCl3), 9.0 (s, 1H), 8.4 (s, 1H), 7.99 (s, 1H), 7.7 (m, 1H), 7.48 (m, 1H), 7.25 (m, 1H), 5.78 (s, 2H), 3.58 (m, 2H), 0.88 (m, 2H), 0 (m, 9H). MS(ESI) m/z:449.2 (M+H)+.

Step C

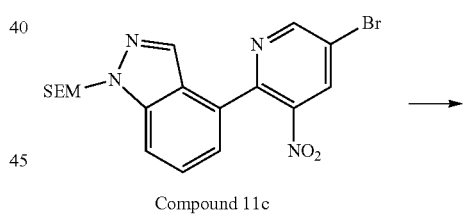

Compound 11c

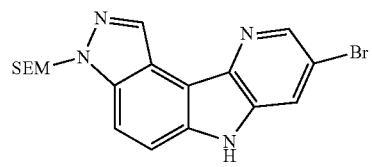

Compound 11d

Compound 11c (12.5 g, 30 mmol) in triethyl phosphite (150 ml) was refluxed for 1 h, and then stirred in an ice bath to give a solid, which was filtered, washed with water and diethyl ether, and dried to give compound 11d.

HNMR (DMSO), 12.0 (s, 1H), 8.75 (s, 1H), 8.64 (s, 1H), 8.37 (s, 1H), 8.06 (d, 1H), 7.85 (d, 1H), 5.99 (s, 2H), 3.68 (m, 2H), 0.94 (m, 2H), 0 (s, 9H). MS (ESI) m/z:417.2 (M+H)+.

Step D

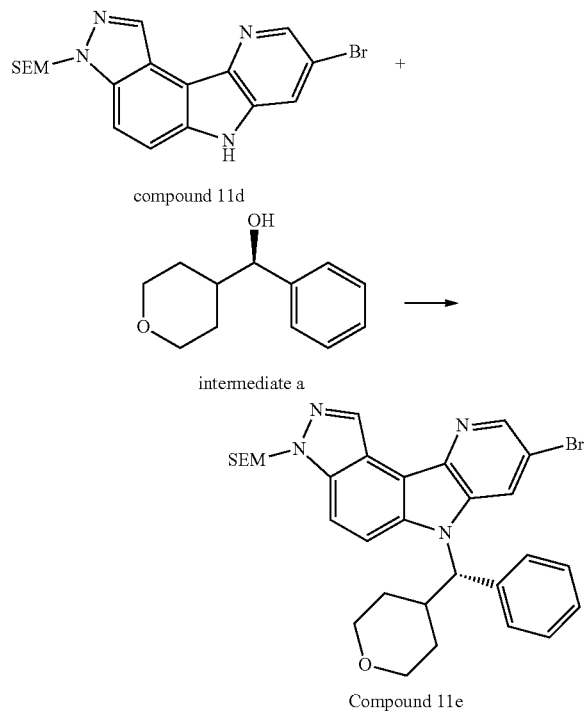

compound 11d intermediate a

Compound 11e

Compound 11d (3 g, 7.2 mmol) was dissolved in DCM (40 ml), and PPh3 (3.7 g, 14.4 mmol) and intermediate a (2.7 g, 14.4 mmol) were added. The reaction mixture was stirred in ice-water bath for 1 h, then a 30 ml solution of DIAD (4 g, 20 mmol) in DCM was slowly added dropwise, and then stirred at room temperature for 2 days, TLC monitored until the reaction is completed. After the solution was dried by suction, the crude was purified by silica gel column chromatography (DCM:MeOH=50:1 to 10:1) to provide compound 11e as a yellow liquid. MS(ESI) m/z:591.2 (M+H)+.

Step E

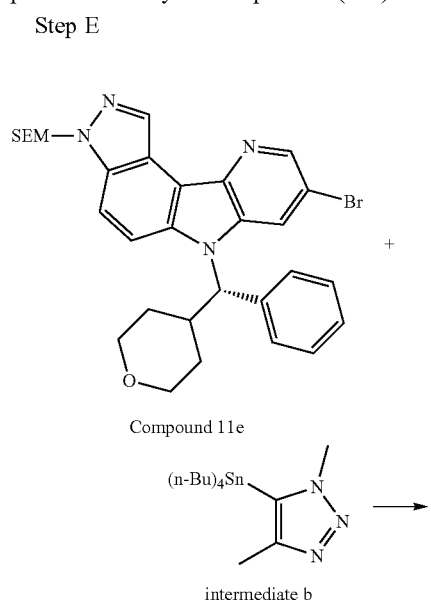

Compound 11e intermediate b

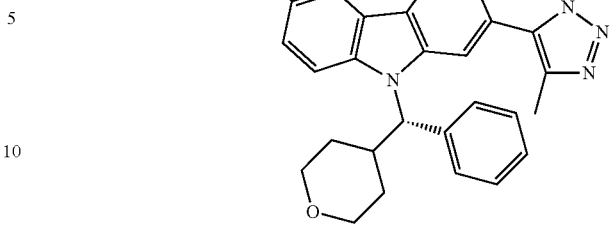

Compound 11f

A mixed solution of compound 11e (1.5 g, 2.5 mmol), intermediate b (2 g, 5 mmol), triethylamine (0.7 ml, 5 mmol) and Pd(dppf)$_2$Cl$_2$ (300 mg) in DMF (20 ml) was flushed with nitrogen. The reaction flask was sealed; the mixture was heated and stirred at 100-140° C. for 4 h, poured into water, and extracted with DCM. The combined organic phases were dried and aspirated to dryness to give crude product purified by silica gel column chromatography (DCM:MeOH=50:1 to 10:1) to provide crude product 11f as a yellow solid.

HNMR (DMSO), 8.7 (s, 1H), 8.5 (s, 1H), 7.8 (m, 2H), 7.7 (s, 1H), 7.45 (m, 2H), 7.2-7.3 (m, 3H), 5.85 (s, 2H), 5.6-5.7 (d, 1H), 4.0-4.1 (m, 4H), 3.0-4.0 (m, 6H), 2.2 (m, 2H), 1.0-2.0 (m, 4H), 0.8-1.0 (m, 2H), 0 (s, 9H). MS(ESI) m/z:608.2 (M+H)+.

Step F

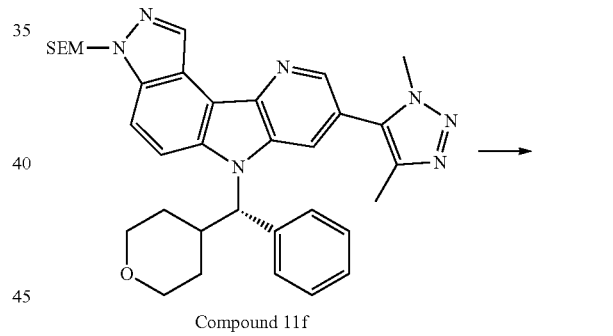

Compound 11f

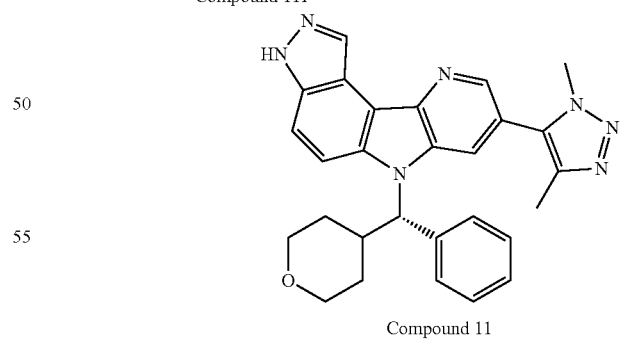

Compound 11

A mixed solution of compound 11f (600 mg, 1 mmol) in DCM (10 ml) was added into TFA (5 ml), and heated under reflux and stirred for 18 h. The crude product was obtained by aspirate and purified by silica gel column chromatography (DCM:MeOH=50:1 to 11:1) to obtain crude product as a yellow solid which was purified by HPLC to give compound 11.

HNMR (CDCl3), 9.18 (s, 1H), 8.87 (s, 1H), 7.95-8.03 (m, 2H), 7.90 (s, 1H), 7.45 (m, 2H), 7.3-7.4 (m, 3H), 5.74 (d, 1H), 4.07-4.09 (m, 1H), 3.95 (s, 3H), 3.83-3.87 (m, 1H), 3.54-3.60 (m, 1H), 3.32-3.38 (m, 1H), 3.13-3.16 (m, 1H), 2.3 (s, 3H), 2.11-2.14 (m, 1H), 1.63-1.67 (m, 1H), 1.4-1.42 (m, 1H), 1.0 (m, 1H). MS(ESI) m/z: 478.7 (M+H)+.

Example 12

Compound 12

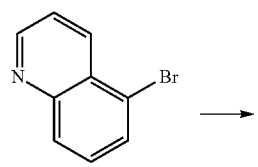

Step A

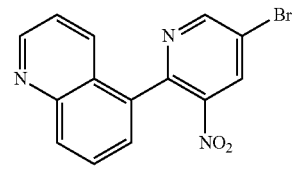

Compound 12a

Compound 12b

To a mixed solution of compound 12a (10 g, 48.4 mmol), bisboronic acid pinacol (14.4 g, 56.8 mmol) and KOAc (9.3 g, 95 mmol) in 1,4-dioxane (200 ml) was added Pd(dppf)$_2$Cl$_2$ (1.5 g), and flushed with nitrogen. The reaction flask was sealed and the reaction was stirred overnight at 85° C. After cooling to room temperature, aqueous Na$_2$CO$_3$ solution (2.5M, 38 ml), Pd(dppf)$_2$Cl$_2$ (1 g) and 2,5-dibromo-3-nitropyridine (16 g, 56.8 mmol) were added. After flushed with nitrogen for 10 minutes, the reaction flask was sealed and the mixture was stirred overnight at 85° C. The reaction was poured into water and extracted with ethyl acetate. The combined organic phase was dried over Na$_2$SO$_4$, dried by suction and purified by silica gel column chromatography (PE:EA=10:1 to 1:1) to provide compound 12b as a yellow solid.

HNMR (CDCl3), 8.9 (m, 2H), 8.47 (s, 1H), 8.2 (d, 1H), 7.85 (m, 1H), 7.72 (m, 1H), 7.4 (m, 1H), 7.35 (m, 1H). MS(ESI) m/z:330.2 (M+H)+.

Step B

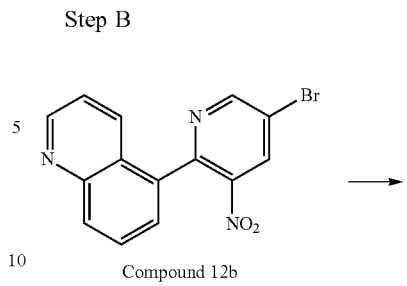

Compound 12b

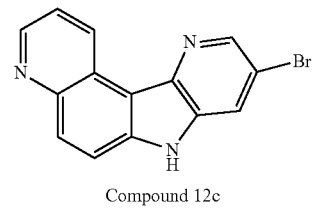

Compound 12c

Compound 12b (10 g, 30 mmol) in triethyl phosphite (100 ml) was refluxed for 1 h, and then stirred in an ice bath to give a solid, which was filtered, washed with water and diethyl ether, and dried to give compound 12c.

HNMR (DMSO), 12.2 (s, 1H), 9.5 (d, 1H), 8.8 (d, 1H), 8.6 (s, 1H), 8.3 (m, 1H), 8.0-8.1 (m, 2H), 7.7 (m, 1H). MS(ESI) m/z:298.2 (M+H)+.

Step C

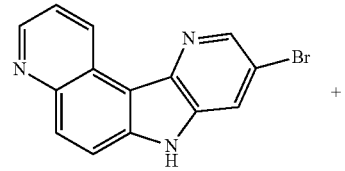

Compound 12c

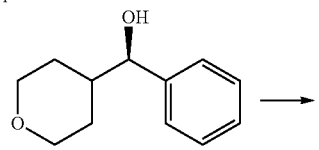

intermediate a

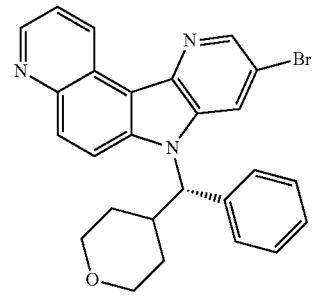

Compound 12d

Compound 12d (3 g, 10 mmol) was dissolved in DCM (100 ml), and PPh3 (5.2 g, 20 mmol) and intermediate a (6.3 g, 33 mmol) were added. The reaction mixture was stirred in ice-water bath for 1 h, then a 50 ml solution of DIAD (4 g, 20 mmol) in DCM was slowly added dropwise, and then stirred at room temperature, TLC monitored until the reaction was completed. After the solution was dried by suction, the crude was purified by silica gel column chromatography (DCM:MeOH=50:1 to 10:1) to provide compound 12d.

HNMR (CDCl3), 9.8 (s, 1H), 8.9 (m, 1H), 8.7 (m, 1H), 8.2 (m, 1H), 8.05 (m, 2H), 7.2-7.6 (m, 6H), 5.5 (d, 1H), 4.05 (m, 1H), 3.8 (m, 1H), 3.5 (m, 1H), 3.35 (m, 1H), 3.15 (m, 1H), 2.0 (m, 1H), 0.8-1.8 (m, 3H). MS(ESI) m/z:472.8 (M+H)+.

Step D

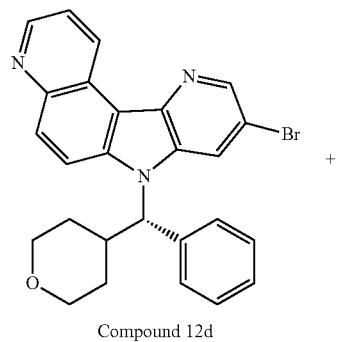

Compound 12d

+

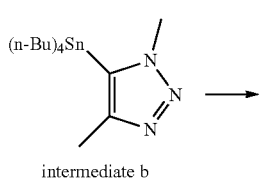

intermediate b

→

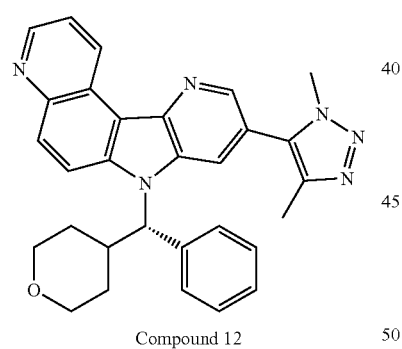

Compound 12

Example 13

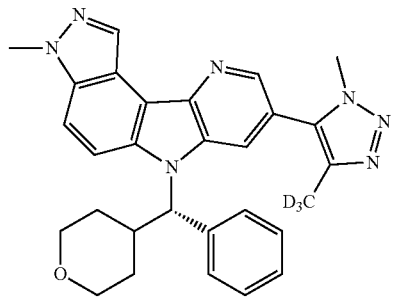

Compound 13

Step A

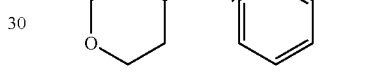

Compound 6d

+

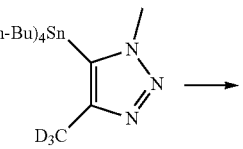

intermediate d

→

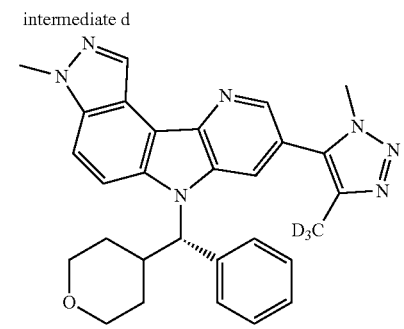

Compound 13

A mixed solution of compound 12d (1.5 g, 3.2 mmol), intermediate b (2.4 g, 6.4 mmol), triethylamine (0.9 ml, 6.4 mmol), Pd(dppf)$_2$Cl$_2$ (300 mg) in DMF (20 ml) was flushed with nitrogen. The reaction flask was sealed, the mixture was heated and stirred at 100-140° C. for 4 h, poured into water, and extracted with DCM. The combined organic phases were dried and aspirated to dryness to give a crude product purified by silica gel column chromatography (DCM:MeOH=50:1 to 10:1) to provide a crude product as a yellow solid and then purified by HPLC to obtain compound 12.

HNMR (DMSO), 9.75 (m, 1H), 8.9 (m, 1H), 8.7 (m, 1H), 8.2 (m, 1H), 7.7 (m, 4H), 7.2-7.4 (m, 4H), 6.0 (d, 1H), 4.0 (s, 3H), 3.2-4.0 (m, 5H), 2.3 (s, 3H), 1.2-1.8 (m, 3H), 0.8-1.0 (m, 1H). MS(ESI) m/z:489.8 (M+H)+.

A mixed solution of compound 6d (1 g, 2.1 mmol), intermediated (1.7 g, 4.3 mmol) (the intermediate d was prepared by the method disclosed in WO2015100282), triethylamine (0.6 ml, 4.2 mmol), and Pd(dppf)$_2$Cl$_2$ (200 mg) in DMF (20 ml) was flushed with nitrogen. The reaction flask was sealed; the mixture was heated and stirred at 100-140° C. for 4 h, poured into water, and extracted with DCM. The combined organic phases were dried and aspirated to dryness to give a crude product purified by silica gel column chromatography (DCM:MeOH=50:1 to 10:1) to provide crude product as a yellow solid and then purified by HPLC to obtain compound 13.

HNMR (CDCl3), 8.7 (s, 1H), 8.6 (s, 1H), 7.8 (m, 1H), 7.6-7.7 (m, 2H), 7.4 (m, 2H), 7.2-7.3 (m, 3H), 5.6 (d, 1H), 4.25 (s, 3H), 4.0-4.1 (m, 1H), 3.9 (s, 3H), 3.8-3.9 (m, 1H), 3.5-3.6 (m, 1H), 3.2-3.5 (m, 1H), 3.0-3.2 (m, 1H), 2.0-2.1 (m, 1H), 1.6-1.8 (m, 1H), 1.2-1.6 (m, 1H), 1.0-1.1 (m, 1H). MS (ESI) m/z: 495.2 (M+H)+.

Example 14

Compound 14

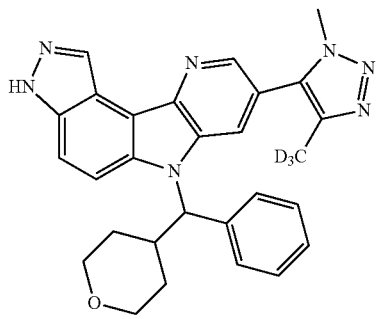

Step A

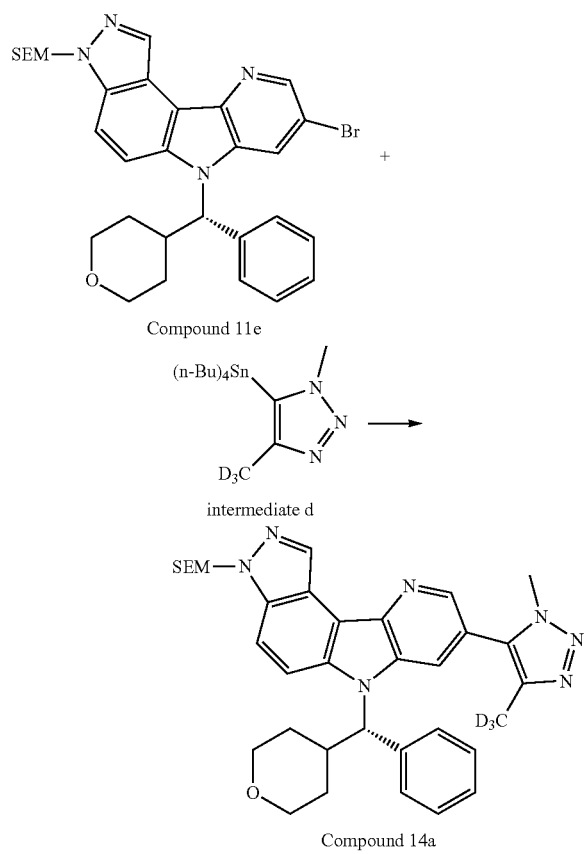

A mixed solution of compound 11e (1.5 g, 2.5 mmol), intermediate d (2 g, 5 mmol), triethylamine (0.7 ml, 5 mmol), and Pd(dppf)$_2$Cl$_2$ (300 mg) in DMF (20 ml) was flushed with nitrogen. The reaction flask was sealed; the mixture was heated and stirred at 100-140° C. for 4 h, poured into water, and extracted with DCM. The combined organic phases were dried and aspirated to dryness to give crude product purified by silica gel column chromatography (DCM:MeOH=50:1 to 10:1) to provide a crude product 14a as a yellow solid. MS(ESI) m/z: 611.2 (M+H)+.

Step B

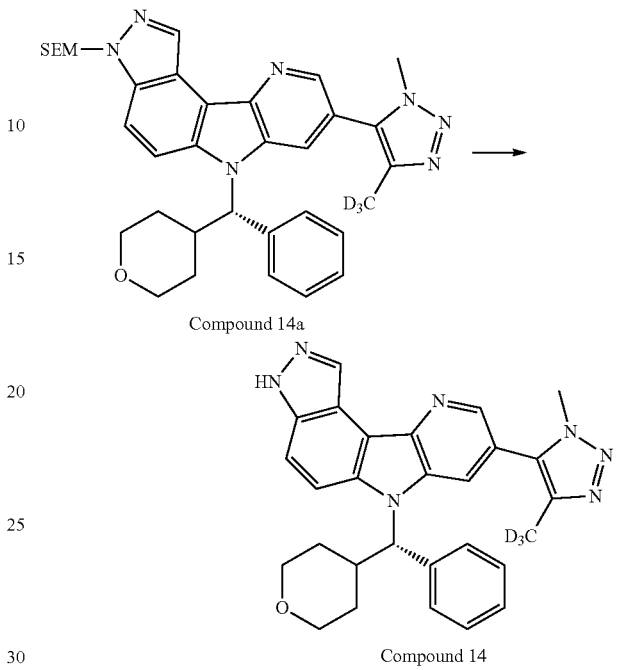

A mixed solution of compound 14a (600 mg, 1 mmol) in DCM (10 ml) was added into TFA (5 ml), and heated under reflux and stirred for 18 h. The crude product was obtained by aspirate and purified by silica gel column chromatography (DCM:MeOH=50:1 to 11:1) to obtain crude product as a yellow solid which was then purified by HPLC to give compound 14.

HNMR (DMSO), 13.4 (s, 1H), 8.5-8.6 (d, 2H), 7.6-7.8 (m, 4H), 7.2-7.3 (m, 3H), 7.19-7.23 (m, 1H), 5.9 (d, 1H), 4.0 (s, 3H), 3.8 (m, 1H), 3.6-3.7 (m, 1H), 3.4-3.5 (m, 2H), 3.2-3.3 (m, 1H), 1.7 (m, 1H), 1.5 (m, 1H), 1.3 (m, 1H), 0.95 (m, 1H). MS(ESI) m/z:481.7 (M+H)+.

Example 15

Detection of TR-FRET BRD4 Activity:

The BRD4 activity assay was performed according to the TR-FRET method in the Cayman kit. Dilute 3×BRD TR-FRET Assay Buffer 1 with ultrapure water to 1×BRD TR-FRET Assay Buffer for further use. 1×BRD TR-FRET Assay Buffer was used to dilute Tb-labeled donor and dye-labeled acceptor in 100-fold. 5 μl of diluted Tb-labeled donor and dye-labeled acceptor were added respectively to the sample well, negative control well and positive control well. The configured 1×BRD TR-FRET Assay Buffer was used to formulate a 10% DMSO solution (excessive DMSO concentration would affect the reaction, and the final concentration of DMSO was controlled at 1%), then test compounds are diluted with 10% DMSO solution to give the compound's initial concentrations of 1 μM and 100 nM, IC50 test was started from 10 μM or 100 μM, diluted in 3-fold to give 8 or 10 concentration points. In addition to the control wells, 2 μl of the diluted test compound solution was added to the wells used, and 2 μl of the previously prepared 10% DMSO solution was added to the control wells. The BET Bromodomain Ligand and Non-acetylated Ligand 1 were respectively diluted in 40 fold with 1×BRD TR-FRET Assay Buffer. 5 μl of diluted BET Bromodomain Ligand was added to sample wells and positive control wells, and 5 μl of diluted non-acetylated ligand 1 was added into the negative control wells. 1×BRD TR-FRET Assay Buffer was used to dilute BRD4 (BD1+BD2) bromodomain protein to 6 ng/μl (18 ng/well), and 3 μl of diluted BRD4 (BD1+BD2) bromodomain protein was added to each well. The plate was sealed and mixed well. The reaction was performed at room temperature for 2 hours, and then fluorescence signals (320 nm stimulation, 665 nm, 615 nm emission) were detected with the ENVISION (Perkinelmer) instrument. The inhibition rate was calculated for each well by positive control wells and negative control wells, and average value was calculated for multiple wells. The results were plotted with Software PRISM 5.0 to fit the half inhibitory activity (IC50) for each test compound, Table 1.

TABLE 1

| Number of the compound | FRET BRD4 $IC_{50}$ (nM) |
| --- | --- |
| 1 | 3.6 |
| 2 | 2.2 |
| 3 | 1.9 |
| 4 | 4.6 |
| 5 | 3.8 |
| 6 | 1 |
| 7 | 5.2 |
| 8 | 2.6 |
| 9 | 3.5 |
| 10 | 1.5 |
| 11 | 1 |
| 12 | 3.2 |
| 13 | 1 |
| 14 | 1 |

Example 16

Cell Activity Detection

MDA-MB-231 cell line was purchased from Shanghai Cell Resource Center of the Chinese Academy of Sciences, and was performed according to the method in the kit of CCK-8. The cells in the logarithmic growth phase were collected, counted, and the cells were re-suspended in complete medium to adjust the cell concentration to a suitable concentration (determined according to cell density optimization test results), inoculated in 96-well plates, and each well was added with 100 μl of cell suspension. Cells were incubated at 37° C., in a 100% relative humidity and 5% $CO_2$ incubator for 24 hours. The compound was diluted to the appropriate effective concentration determined with medium and the cells were added by 25 μl/well. The final concentration of the compound was diluted to from 1 μM to 0 μM graded in three-fold dilution to give 10 concentration points. The cells were incubated at 37° C., in a 100% relative humidity and 5% $CO_2$ incubator for 72 hours. 1/10 volume of CCK-8 was added directly to the cell culture medium and incubated in a 37° C. incubator for 2-4 hours. The absorbance at 450 nm was determined on a SpectraMax M5 Microplate Reader after gentle shaking. Absorbance at 650 nm was taken as the reference. The IC50 curve fitting was performed using soft Graphpad Prism 5 and the IC50 value was calculated.

H211 and H187 cell lines were purchased from ATCC and tested in accordance with the Alamar-Blue test kit instructions. The drugs were dissolved in 50 mM stock solution with DMSO and stored in a freezer at −20° C. The test drug stock solution was serially diluted with DMSO graded in a ratio of 1:3. Then DMSO diluted drug was serially diluted into a drug solution in 10× final concentration with cell complete culture medium. The 96-well cell culture plate was removed from the incubator, and 10 μl of culture medium containing a series of different concentrations of drug (10× final concentration) was added to a 96-well plate, and incubated at 37° C. for 72 h in CO2 incubator. The inhibition rate was plotted using GraphPad Prism 5.0 and MATILAB software by a non-linear regression method to obtain a series of dose-response curves from which the IC50 of the test sample was obtained, Table 2.

TABLE 2

| Number of the compound | MDA-MB-231 $IC_{50}$ (nM) | H211 $IC_{50}$ (nM) | H187 $IC_{50}$ (nM) |
| --- | --- | --- | --- |
| 1 | ND | 7.2 | 21 |
| 2 | ND | 8.5 | 19 |
| 3 | ND | 5.2 | 35 |
| 4 | ND | 11.2 | 37 |
| 5 | ND | 29.5 | 35 |
| 6 | 1.6 | 2 | 5.5 |
| 7 | 4.6 | 3.5 | 6.5 |
| 8 | 3.2 | 4.2 | 6.5 |
| 9 | ND | 6.7 | 7 |
| 10 | 8.1 | 32 | 8.5 |
| 11 | 3.7 | 4.2 | 5.5 |
| 12 | ND | 12 | 7.5 |
| 13 | 1.8 | 2 | 5.5 |
| 14 | 3.5 | 4 | 5.5 |

ND: No detection.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

What I claimed is:

1. A carboline derivative selected from the group consisting of

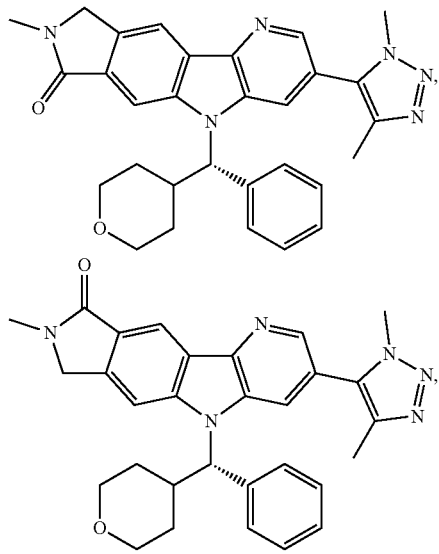

-continued

-continued
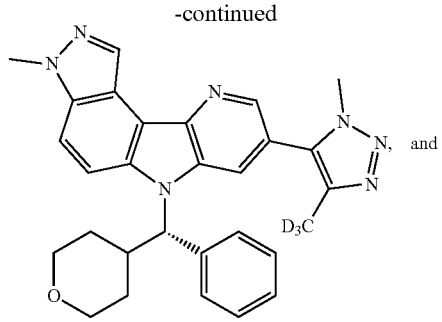
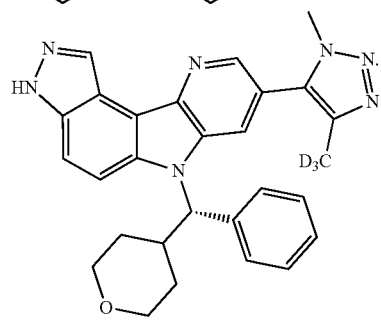
or a salt thereof.
2. A pharmaceutical composition, comprising: (i) a therapeutically effective amount of the compound of claim 1, or a pharmaceutically acceptable salt thereof, and (ii) a pharmaceutically acceptable carrier.
* * * * *